(12) United States Patent
Arinobe et al.

(10) Patent No.: US 11,938,305 B2
(45) Date of Patent: Mar. 26, 2024

(54) CAP, SYRINGE ASSEMBLY AND MANUFACTURING METHOD THEREOF

(71) Applicant: TERUMO KABUSHIKI KAISHA, Tokyo (JP)

(72) Inventors: Manabu Arinobe, Kanagawa (JP); Yusuke Hyakkan, Kanagawa (JP); Eri Oya, Kanagawa (JP); Taeko Masuda, Kanagawa (JP); Junichi Ogawa, Yamanashi (JP); Yoichiro Iwase, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 860 days.

(21) Appl. No.: 17/024,957

(22) Filed: Sep. 18, 2020

(65) Prior Publication Data

US 2021/0001049 A1  Jan. 7, 2021

Related U.S. Application Data

(63) Continuation of application No. PCT/JP2019/011785, filed on Mar. 20, 2019.

(30) Foreign Application Priority Data

Mar. 20, 2018  (JP) ................. 2018-051900

(51) Int. Cl.
   *A61M 5/31*  (2006.01)
(52) U.S. Cl.
   CPC ....... *A61M 5/31* (2013.01); *A61M 2005/3104* (2013.01); *A61M 2207/00* (2013.01)

(58) Field of Classification Search
   CPC ............ A61M 5/31; A61M 2005/3103; A61M 2005/3104; A61M 2005/3107
   See application file for complete search history.

(56) References Cited

U.S. PATENT DOCUMENTS

| | | | |
|---|---|---|---|
| 5,226,894 A | * | 7/1993 | Haber ................. A61M 5/3243 604/240 |
| 5,741,236 A | | 4/1998 | Kakiuti |

(Continued)

FOREIGN PATENT DOCUMENTS

| | | |
|---|---|---|
| CN | 107596504 A | 1/2018 |
| EP | 3 269 418 A1 | 1/2018 |

(Continued)

OTHER PUBLICATIONS

International Search Report (PCT/ISA/210) dated Jun. 25, 2019, by the Japanese Patent Office as the International Searching Authority for International Application No. PCT/JP2019/011785.

(Continued)

*Primary Examiner* — Dung T Ulsh
(74) *Attorney, Agent, or Firm* — BUCHANAN INGERSOLL & ROONEY PC

(57) ABSTRACT

A syringe assembly includes a plate-shaped seal member that seals a distal opening of a distal nozzle portion of a syringe; and a tubular cover member. The cover member has a base portion and a mounting portion. The mounting portion has two claw portions, two first column portions arranged on both sides of one of the two claw portions, and two second column portions arranged on both sides of the other of the two claw portions. An outer peripheral portion of the mounting portion has two outer peripheral notch portions. An inner peripheral portion of the mounting portion has two inner peripheral recessed portions.

18 Claims, 16 Drawing Sheets

(56) References Cited

U.S. PATENT DOCUMENTS

| | | | |
|---|---|---|---|
| 2007/0112314 A1* | 5/2007 | Harding | A61M 39/045 264/239 |
| 2013/0030414 A1* | 1/2013 | Gardner | A61M 39/20 604/533 |
| 2013/0046253 A1 | 2/2013 | Yavorsky et al. | |
| 2014/0052074 A1* | 2/2014 | Tekeste | A61M 39/162 604/199 |
| 2015/0165127 A1* | 6/2015 | Haefele | B65B 7/01 220/254.1 |
| 2015/0196720 A1 | 7/2015 | Okihara et al. | |
| 2016/0045629 A1* | 2/2016 | Gardner | A61B 90/70 422/292 |
| 2016/0144118 A1* | 5/2016 | Solomon | A61M 5/30 206/370 |
| 2019/0282795 A1* | 9/2019 | Fangrow | A61M 25/0082 |
| 2019/0298986 A1 | 10/2019 | Rivier et al. | |

FOREIGN PATENT DOCUMENTS

| | | |
|---|---|---|
| JP | 4759630 B2 | 6/2011 |
| WO | 2009/096227 A1 | 8/2009 |
| WO | 2013/047042 A1 | 4/2013 |
| WO | 2015033953 A1 | 3/2015 |
| WO | 2018168989 A1 | 9/2018 |

OTHER PUBLICATIONS

Written Opinion (PCT/ISA/237) dated Jun. 25, 2019, by the Japanese Patent Office as the International Searching Authority for International Application No. PCT/JP2019/011785.

Office Action (The First Office Action) dated Jan. 18, 2022, by the National Intellectual Property Administration P.R. China in corresponding Chinese Patent Application No. 201980020446.1 and an English Translation of the Office Action. (20 pages).

The extended European Search Report dated Apr. 7, 2021, by the European Patent Office in corresponding European Patent Application No. 19771933.9-1122. (12 pages).

* cited by examiner

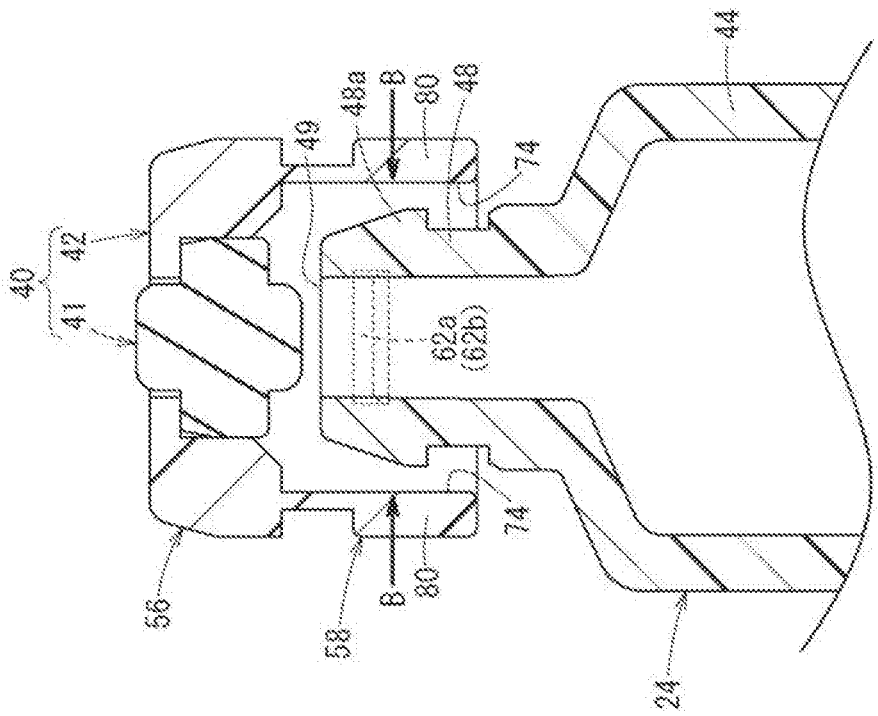
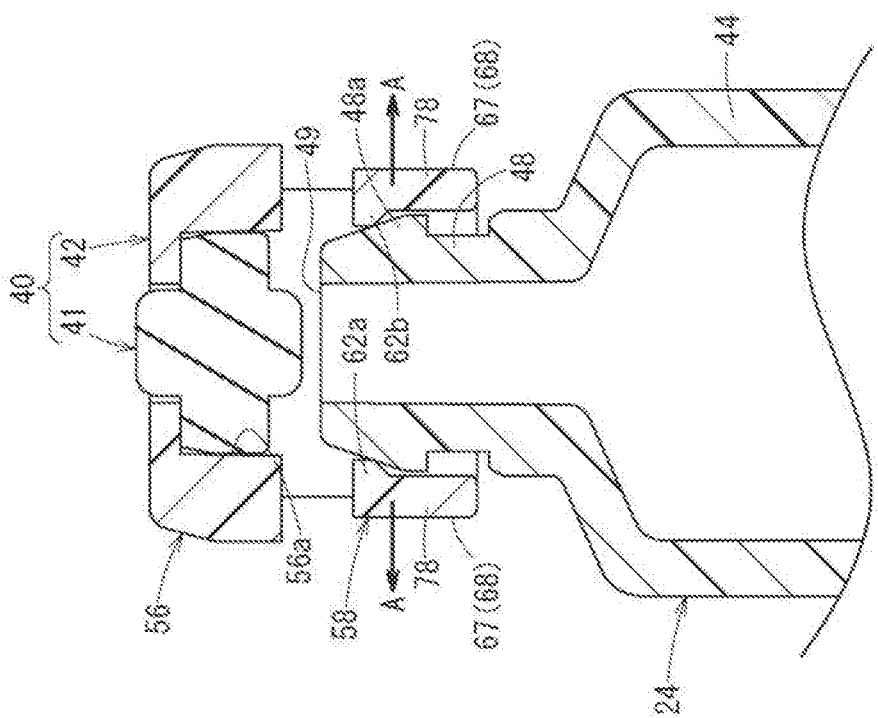

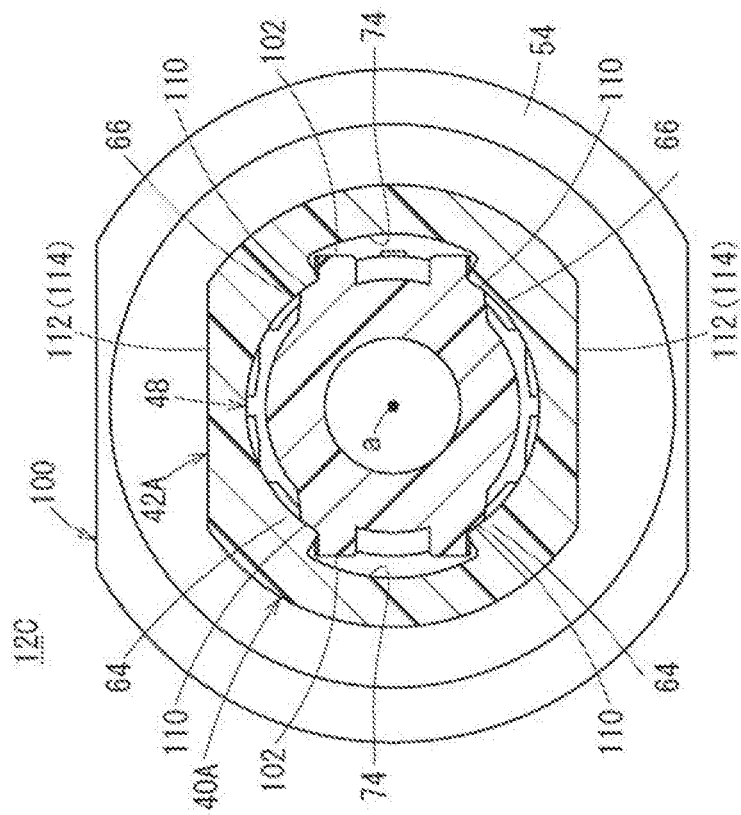

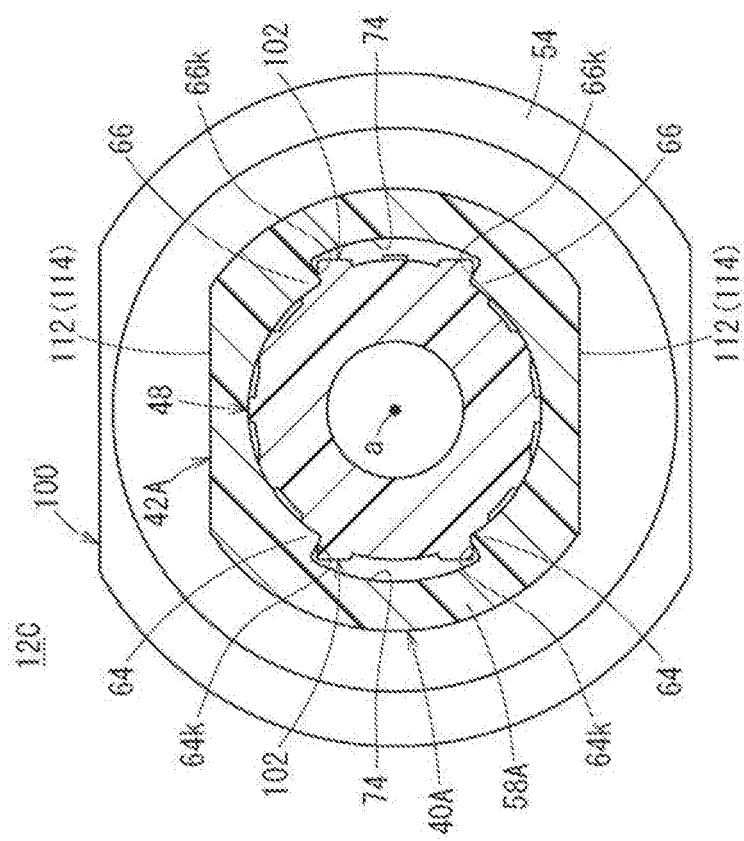
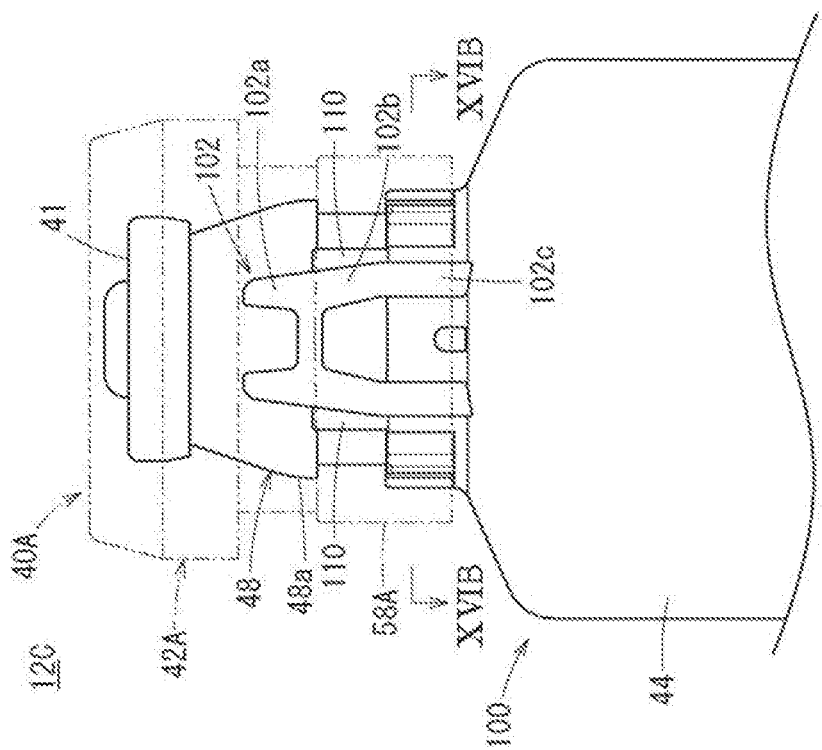

CAP, SYRINGE ASSEMBLY AND MANUFACTURING METHOD THEREOF

CROSS-REFERENCES TO RELATED APPLICATIONS

This application is a continuation of International Application No. PCT/JP2019/011785 filed on Mar. 20, 2019, which claims priority to Japanese Patent Application No. 2018-051900 filed on Mar. 20, 2018, the entire content of each of which is incorporated herein by reference.

FIELD OF THE INVENTION

The present invention generally relates to a cap, a syringe assembly, and a manufacturing method therefor.

BACKGROUND DISCUSSION

A conventional syringe pump type drug solution administration device, which administers a drug solution charged in a tubular body into a living body under pressing action of a plunger, is disclosed, for example, in Japanese Patent No. 4759630. The drug solution administration device includes a syringe assembly filled with a drug solution. The syringe assembly includes a syringe having a distal nozzle portion and a cap fixed to the distal nozzle portion. The cap has a seal member made of an elastic body that seals a distal opening of the distal nozzle portion, and a hard cover member that covers the seal member.

SUMMARY

When the cap is attached to the distal nozzle portion in an assembly step of the syringe assembly, an excessive load is applied to a claw portion formed on an inner peripheral portion of the cover member of the cap so that the claw portion is likely to be partially or completely scraped off. When the claw portion is partially or completely scraped off, the cap easily comes off from the syringe after the assembly.

Disclosed here is a cap that does not easily come off from a distal nozzle portion of a syringe, a syringe assembly including the cap, and a manufacturing method for the syringe assembly.

A tubular cap according to embodiments disclosed here is mountable to a distal nozzle portion of a syringe, and includes: a plate-shaped sealing member that has elasticity and seals a distal opening of the distal nozzle portion; and a tubular cover member that holds the seal member and is harder than the seal member. The cover member has a base portion provided at a distal end of the cover member, and a tubular mounting portion that extends in a proximal direction from the base portion along an axis of the cap and covers the distal nozzle portion. The base portion has a holding portion that holds the seal member, and a through-hole that communicates with the holding portion and exposes a distal surface of the seal member. The mounting portion has: two claw portions that are arranged at positions separated from the holding portion in the proximal direction, protrude inward from an inner peripheral surface of the mounting portion, and oppose each other; two first column portions that are arranged on both sides of one of the two claw portions in a circumferential direction of the mounting portion and extend in the proximal direction along the axis of the cap; and two second column portions that are arranged on both sides of another of the two claw portions in the circumferential direction of the mounting portion and extend in the proximal direction along the axis of the cap. An outer peripheral portion of the mounting portion has two outer peripheral notch portions arranged between the two first column portions and between the two second column portions, respectively, so as to face opposite directions. Portions of the mounting portion where the two outer peripheral notch portions are provided have a smaller radial thickness than the two first column portions and the two second column portions, and each distance from the axis of the two outer peripheral notch portions is shorter than a distance from the axis of each outer peripheral surface of the two first column portions and the two second column portions. An inner peripheral portion of the mounting portion has two inner peripheral recessed portions which are arranged to oppose each other between the two first column portions and between the two second column portions, respectively, and are recessed radially outward from inner peripheral surfaces of the two first column portions and the two second column portions.

According to the cap configured as described above, the outer peripheral portion of the mounting portion has the two outer peripheral notch portions, the inner peripheral portion of the mounting portion has the two inner peripheral recessed portions, and the two claw portions are provided at positions opposite to the two outer peripheral notch portions. Thus, the mounting portion is deformed outward at the two outer peripheral notch portions and is deformed inward at the two inner peripheral recessed portions when mounting the cap to the distal nozzle portion of the syringe. As a result, the mounting portion of the cap is deformed into an elliptical shape, an excessive load is not applied to the two claw portions during the assembly, and it is possible to suppress the two claw portions from being scrapped partially or completely scraped off. Therefore, the cap is reliably prevented from coming off from the distal nozzle portion of the syringe. Further, the cap includes the four column portions (two first column portions and two second column portions), and thus, is barely deformed during sterilization (i.e., largely holds its shape) even when a sterilization process involving heating is performed on the syringe assembly including the cap. For this reason, the cap is reliably prevented from coming off from the distal nozzle portion of the syringe even after the sterilization involving heating.

The inner peripheral portion of the mounting portion may have two proximal abutment portions arranged between the two first column portions and between the two second column portions, respectively, so as to oppose each other. The two proximal abutment portions may abut on the outer peripheral surface of the distal nozzle portion to prevent the cap from being inclined with respect to the distal nozzle portion.

With this configuration, rattling of the cap after the assembly can be suppressed, and thus, it is possible to suppress a variation in pressure resistance of the cap (which could result in undesired leakage of a drug solution) and a variation in pulling strength (which could result in undesired removal of the cap).

The inner peripheral surfaces of the two first column portions and the two second column portions may abut on the outer peripheral surface of the distal nozzle portion to prevent the cap from being inclined with respect to the distal nozzle portion.

With this configuration, the rattling of the cap after the assembly can be suppressed, and thus, it is possible to suppress the variation in pressure resistance of the cap and the variation in pulling strength.

The base portion may have a distal abutment portion, which abuts on the outer peripheral surface of the distal nozzle portion to prevent the cap from being inclined with respect to the distal nozzle portion, at a proximal end of the holding portion.

With this configuration, the rattling of the cap after the assembly can be suppressed, and thus, it is possible to suppress the variation in pressure resistance of the cap and the variation in pulling strength.

The mounting portion may have, at proximal ends of the two claw portions, two first side wall portions having the two outer peripheral notch portions and two second side wall portions having the two inner peripheral recessed portions. Thicknesses of the first column portion and the second column portion in a radial direction of the mounting portion may be 1.25 to 3.0 times of thicknesses of the first side wall portion and the second side wall portion in the radial direction of the mounting portion.

With this configuration, the mounting portion is more likely to be deformed when the cap is mounted on the distal nozzle portion, and is reliably prevented from coming off after the mounting of the cap.

The thicknesses of the first side wall portion and the second side wall portion may be 0.5 to 1.5 mm.

With this configuration, the mounting portion is more likely to be deformed when the cap is mounted on the distal nozzle portion.

The thicknesses of the first column portion and the second column portion may be 0.7 to 2.5 mm.

With this configuration, it is more difficult for the cap to come off after the cap is mounted on the distal nozzle portion.

Each of the two outer peripheral notch portions may extend from the respective distal ends of the two claw portions to the proximal end of the mounting portion.

With this configuration, the mounting portion is more reliably deformed.

Each of the two inner peripheral recessed portions may extend from the distal end to the proximal end of the mounting portion.

With this configuration, the mounting portion is more reliably deformed.

The base portion may have a plurality of ribs which protrude from an inner peripheral surface of the holding portion, extend along the axis of the cap, and fit with an outer peripheral surface of the seal member. Each of the plurality of ribs may have, at a proximal end, an inclined portion whose protruding height gradually decreases toward the proximal end.

Since the plurality of ribs are provided on the inner peripheral surface of the holding portion, the seal member can be reliably held in the holding portion in the state before attaching the cap to the distal nozzle portion of the syringe, and thus, the mounting step of the cap can be efficiently performed.

The two outer peripheral notch portions may be two outer peripheral recessed portions that are recessed radially inward from the outer peripheral surfaces of the two first column portions and the two second column portions.

The two outer peripheral notch portions may be two flat portions parallel to the axis of the cap.

Further disclosed is a syringe assembly including: a syringe having a distal nozzle portion; and a cap mounted to the distal nozzle portion of the syringe. The cap is the above-described cap. The distal nozzle portion has an engagement projected portion on an outer peripheral surface. As the claw portions of the mounting portion engage with the engagement projected portion, the cap is mounted to the distal nozzle portion, and the distal opening of the distal nozzle portion is sealed by the seal member.

Further disclosed is a syringe assembly including: a syringe having a distal nozzle portion; and a cap mounted to the distal nozzle portion of the syringe. The cap is any cap described above. The syringe has two anti-rotation projected portions that prevent the cap from rotating in a circumferential direction with respect to the distal nozzle portion. The two anti-rotation projected portions protrude from an outer peripheral portion of the distal nozzle portion to a radially outside of the distal nozzle portion, are inserted between the two first column portions and the two second column portions, respectively, and engage with corner portions of the two first column portions and corner portions of the two second column portions, respectively.

The syringe may have four fitting projected portions which are adjacent to both sides of the two anti-rotation projected portions in the circumferential direction of the distal nozzle portion, protrude radially outward from the outer peripheral portion of the distal nozzle portion, and fit with inner surfaces of the two first column portions and inner surfaces of the two second column portions, respectively.

The two anti-rotation projected portions may respectively have two distal projected portions forming distal sides of the two anti-rotation projected portions, two proximal projected portions forming proximal sides of the two anti-rotation projected portions, and two intermediate projected portions forming spaces between each of the two distal projected portions and each of the two proximal projected portions of the two anti-rotation projected portions. Widths of the two proximal projected portions along the circumferential direction of the distal nozzle portion may be respectively larger than widths of the two distal projected portions along the circumferential direction of the distal nozzle portion. At least the two intermediate projected portions of the two anti-rotation projected portions may respectively have two inclined guide portions whose widths along the circumferential direction of the distal end nozzle portion increase toward a proximal direction. Distal widths of distal ends of the two intermediate projected portions along the circumferential direction of the distal nozzle portion and the widths of the two distal projected portions along the circumferential direction of the distal nozzle portion may be smaller than corresponding widths along the circumferential direction of the corresponding distal nozzle portion between the two first column portions and the two second column portions.

Further disclosed is a manufacturing method for a syringe assembly including: preparing a syringe that includes a distal nozzle portion having an engagement projected portion provided on an outer peripheral surface and a distal opening; preparing a plate-shaped seal member having elasticity; preparing a cover member that is made of a harder material than the seal member and includes: a base portion provided at a distal end; and a tubular mounting portion extending from the base portion in a proximal direction along an axis of a cap, the base portion having a holding portion that holds the seal member and a through-hole that communicates with the holding portion and exposes a distal surface of the seal member, the mounting portion having two claw portions that are arranged at positions separated from the holding portion in the proximal direction, protrude inward from an inner peripheral surface of the mounting portion, and oppose each other; inserting the distal nozzle portion into the mounting portion of the cover member in which the seal member is held in the holding portion; and pushing the distal nozzle part into the mounting portion until the engaging projected portion passes over the two claw portions toward the distal direction to seal the distal opening of the distal nozzle portion with the seal member, and mounting the cap on the distal nozzle portion. The mounting portion includes: two first reinforcing portions arranged on both sides of one of the two claw portions in a circumferential direction of the mounting portion; two second reinforcing portions arranged on both sides of another of the two claw portions in the circumferential direction of the mounting portion; two first deformation promoting portions which are arranged respectively between the two first reinforcing portions and between the two second reinforcing portions and oppose each other; and two second deformation promoting portions which are arranged between each of the two first reinforcing portions and each of the two second reinforcing portions and oppose each other. When the engagement projected portion passes over the two claw portions, the two first deformation promoting portions are deformed radially outward, and the two second deformation promoting portions are deformed radially inward so as to make a distance between the two claw portions substantially equal to an outer diameter of the engagement projected portion.

According to the cap, the syringe assembly, and the manufacturing method according to the present disclosure, the cap is reliably prevented from coming off from the distal nozzle portion of the syringe.

BRIEF DESCRIPTION OF THE DRAWINGS

FIG. 8A is a first cross-sectional view for describing a manufacturing method for a syringe assembly according to an embodiment. FIG. 8B is a second cross-sectional view illustrating the manufacturing method for the syringe assembly according to the embodiment.

FIG. 15A is a side view of the syringe assembly illustrated in FIG. 11 in a provisionally assembled state. FIG. 15B is a cross-sectional view of the syringe assembly taken along line XVB-XVB in FIG. 15A.

FIG. 16A is a side view of the syringe assembly illustrated in FIG. 11 in an assembled state. FIG. 16B is a cross-sectional view of the syringe assembly taken along line XVIB-XVIB in FIG. 16A.

DETAILED DESCRIPTION

Figure 1:
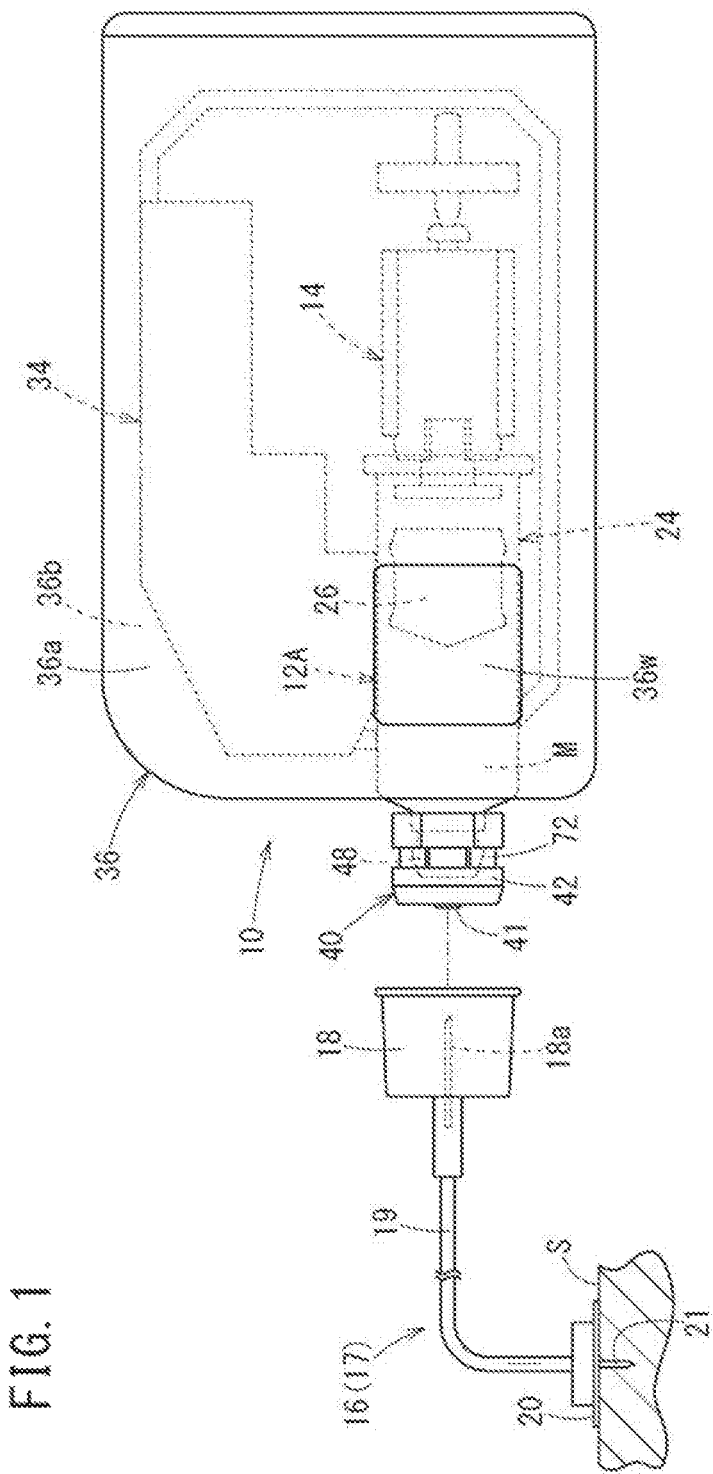
FIG. 1 is a schematic diagram of a drug solution administration device including a syringe assembly according to a first embodiment.

Set forth below with reference to the accompanying drawings is a detailed description of embodiments of a cap, syringe assembly and manufacturing method representing examples of the inventive cap, syringe assembly and manufacturing method. The same or similar elements in a second embodiment as those of a first embodiment will be denoted by the same reference numerals, and a detailed description thereof will be omitted.

First Embodiment

A drug solution administration device 10 illustrated in FIG. 1 is used to administer a drug solution M into a living body. The drug solution administration device 10 continuously administers the drug solution M charged in a syringe assembly 12A into the living body under pressing action of a plunger assembly 14 for a relatively long time (for example, about several minutes to several hours). The drug solution administration device 10 may intermittently administer the drug solution M into the living body. Examples of the drug solution M include a protein preparation, a narcotic analgesic, a diuretic, and the like.

When using the drug solution administration device 10, for example, a patch-type needle-attached tube 17 is connected to the drug solution administration device 10 as an administration tool 16, and the drug solution M discharged from the syringe assembly 12A is injected into a body of a patient via the needle-attached tube 17 as illustrated in FIG. 1. The needle-attached tube 17 includes: a connector 18 that can be connected to a distal nozzle portion 48 of the syringe assembly 12A; a liquid supply tube 19 having one end connected to the connector 18 and having flexibility; a patch portion 20 that is connected to the other end of the liquid supply tube 19 and can be stuck to the skin S; and a puncture needle 21 protruding from the patch portion 20. The puncture needle 21 punctures substantially perpendicularly to the skin S. Incidentally, the puncture needle 21 may be one that obliquely punctures the skin S.

Incidentally, the administration tool 16 connected to the drug solution administration device 10 is not limited to the patch-type needle-attached tube 17 described above, and may be, for example, one having a puncture needle (a winged needle or the like) connected to a distal end of the liquid supply tube 19. Alternatively, the administration tool 16 may be a bent needle that can be connected to the distal nozzle portion 48 of the syringe assembly 12A without the liquid supply tube 19. In this case, the bent needle is bent, for example, approximately 90° downward from the distal nozzle portion 48 of the syringe assembly 12A, and punctures perpendicularly to the skin S as the drug solution administration device 10 is fixed (attached) to the skin S. Further, the distal nozzle portion 48 of the syringe assembly 12A, the administration tool 16, and a part of the needle may be present inside the syringe assembly 12A, and a distal end of the needle may protrude from the syringe assembly 12A. Even in this case, the needle punctures perpendicularly to the skin S as the drug solution administration device 10 is fixed (attached) to the skin S.

Figure 2:
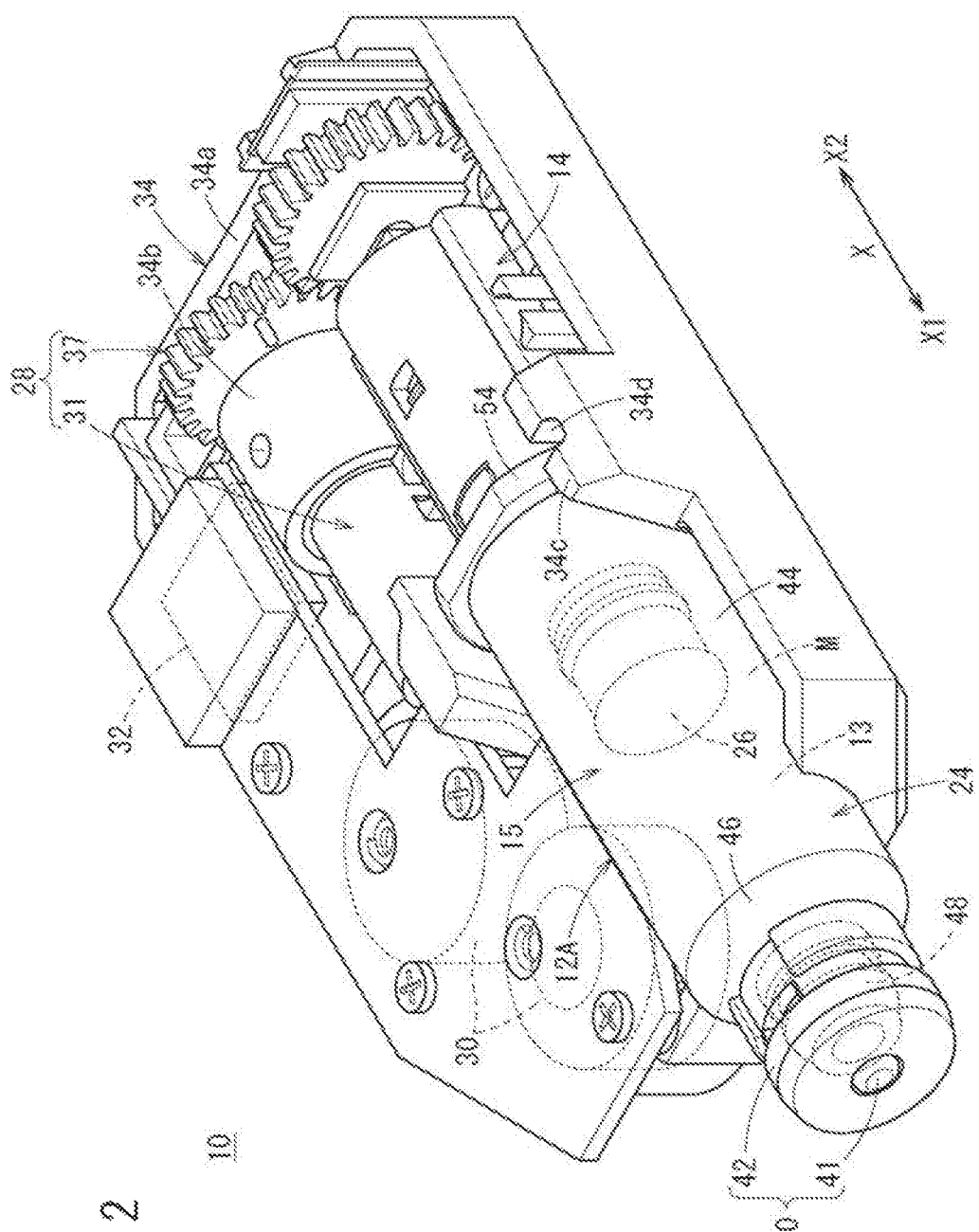
FIG. 2 is a perspective view of the drug solution administration device from which a housing has been removed.

As illustrated in FIG. 1 or 2, the drug solution administration device 10 includes: the syringe assembly 12A having a syringe 24 filled with the drug solution M; a gasket 26 slidably arranged in the syringe 24; the plunger assembly 14 that is stretchable in the axial direction (arrow X direction) and can press the gasket 26 in the distal direction (arrow X1 direction); a drive mechanism 28 that drives the plunger assembly 14; a battery 30 that supplies electric power necessary for the operation of the drug solution administration device 10; a control unit 32 that controls the drive mechanism 28; a chassis structure 34 that supports the syringe assembly 12A, the plunger assembly 14, and the drive mechanism 28; and a housing 36 that houses these.

As illustrated in FIG. 2, the syringe assembly 12A includes the syringe 24 having the distal nozzle portion 48 and a cap 40 attached to the distal nozzle portion 48 of the syringe 24.

The syringe 24 is formed in a hollow cylindrical shape. Specifically, the syringe 24 includes: a body portion 44 having a lumen 13 capable of being filled with the drug solution M; a shoulder portion 46 reduced in diameter from a distal end of the body portion 44; the distal nozzle portion 48 protruding in the distal direction from the shoulder portion 46; and a flange portion 54 protruding outward from an outer peripheral surface of the body portion 44. The inside of the syringe 24 is filled with the drug solution M in advance. The syringe 24 may be made of a transparent material.

Figure 3:
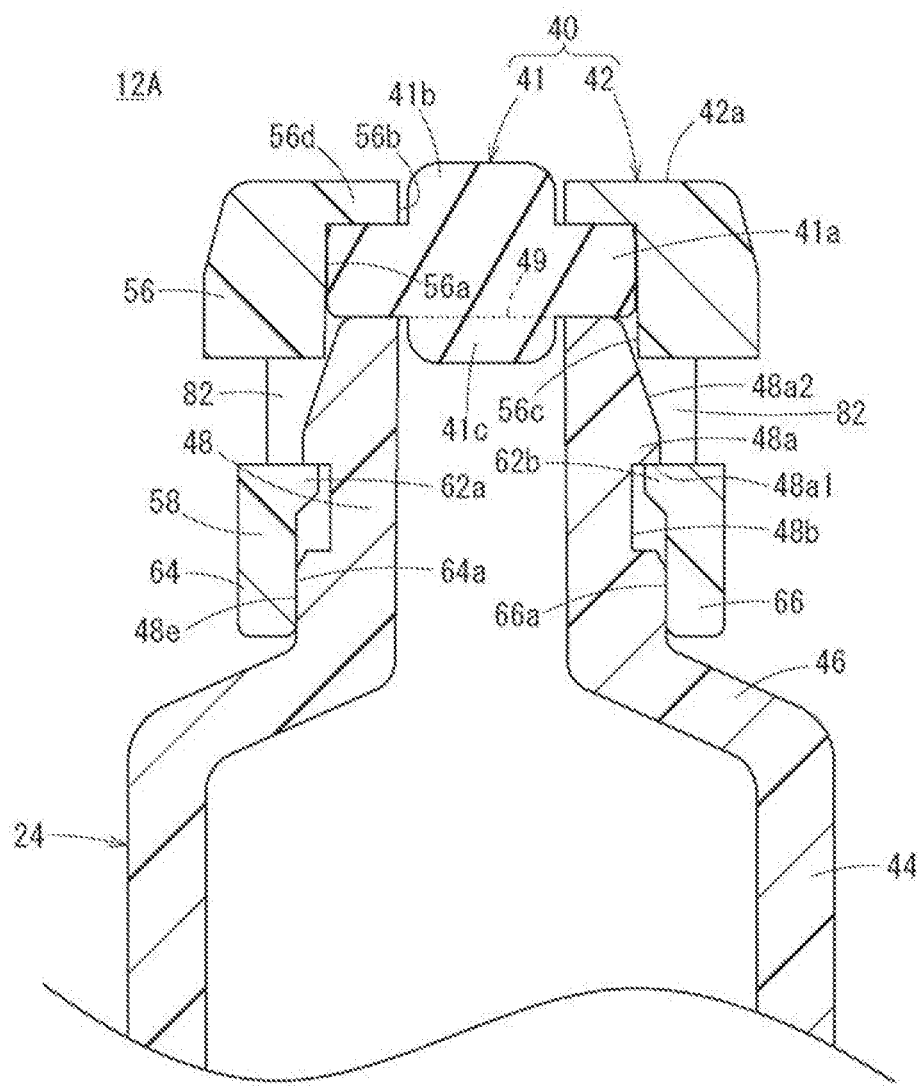
FIG. 3 is a cross-sectional view of the distal side of a syringe assembly illustrated in FIG. 2.

As illustrated in FIG. 3, a distal portion of the distal nozzle portion 48 is provided with an engagement projected portion 48a. The engagement projected portion 48a is formed in an annular shape that protrudes radially outward and extends to form an arc shape in the circumferential direction. The engagement projected portion 48a includes: a locking surface 48a1 on which claw portions 62a and 62b, which will be described later, of the cap 40 are locked; and an inclined surface 48a2 which is formed on the distal side of the locking surface 48a1 and reduced in diameter toward the distal direction. The locking surface 48a1 is a flat surface perpendicular to an axis of the distal nozzle portion 48. On an outer peripheral portion of the distal nozzle portion 48, an annular groove 48b that is recessed radially inward is formed on the proximal side of the engagement projected portion 48a.

An anti-rattling projected portion 48e that prevents rattling of the cap 40 is provided on the outer periphery of a proximal portion of the distal nozzle portion 48. The anti-rattling projected portion 48e is formed in an annular shape that bulges radially outward and extends to form an arc shape in the circumferential direction. An outer peripheral surface of the anti-rattling projected portion 48e extends along the axis of the distal nozzle portion 48. A proximal end of the anti-rattling projected portion 48e is connected to a distal end of the shoulder portion 46.

The cap 40 is made of an elastic resin material, such as a rubber material and an elastomer material, and includes: a plate-shaped seal member 41 that seals a distal opening 49 of the distal nozzle portion 48; and a tubular cover member 42 that holds the seal member 41 and is harder than the seal member 41.

The seal member 41 is fixed to the distal nozzle portion 48 of the syringe assembly 12A by the cover member 42. The seal member 41 is held between a distal surface of the distal nozzle portion 48 and a distal end of the cover member 42 in the state of being elastically compressed in the axial direction. The seal member 41 is formed in a disc shape.

The seal member 41 includes: a seal body portion 41a forming a central portion in the thickness direction; a distal projected portion 41b protruding in the distal direction from a distal surface of the seal body portion 41a; and a proximal projected portion 41c protruding in the proximal direction from a proximal surface of the seal body portion 41a. The distal projected portion 41b slightly protrudes in the distal direction from a distal surface 42a of the cover member 42.

Incidentally, a distal surface of the distal projected portion 41b may be located at the same axial position as the distal surface 42a of the cover member 42 or on the proximal side of the distal surface 42a. The seal member 41 is punctured by a needle 18a provided in the connector 18 when the connector 18 illustrated in FIG. 1 is connected to the distal nozzle portion 48.

Figure 4:
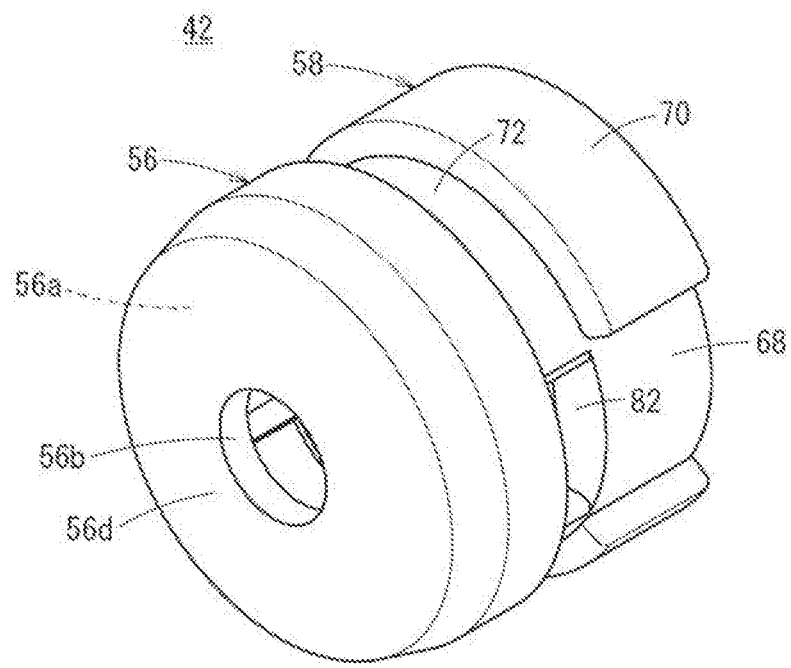
FIG. 4 is a perspective view of a cover member viewed from the distal side.

As illustrated in FIGS. 3 and 4, the cover member 42 includes: a base portion 56 provided at the distal end of the cover member 42; and a tubular (cylindrical) mounting portion 58 that extends from the base portion 56 in the proximal direction along the axis of the cap 40 and covers the distal nozzle portion 48. The base portion 56 includes: a holding portion 56a that holds the seal member 41; and a through-hole 56b that communicates with the holding portion 56a and exposes a distal surface of the seal member 41. The holding portion 56a is formed in a substantially circular shape.

The through-hole 56b is a circular hole portion and is formed coaxially with the holding portion 56a and has a smaller diameter than the holding portion 56a. The through-hole 56b is formed in a distal wall 56d of the base portion 56. As illustrated in FIG. 3, the distal projected portion 41b of the seal member 41 is inserted into the through-hole 56b. The distal surface of the seal member 41 is exposed from the through-hole 56b of the cover member 42.

A distal abutment portion 56c, which abuts on the outer peripheral surface of the distal nozzle portion 48 to prevent the cap 40 from being inclined with respect to the distal nozzle portion 48, is provided at a proximal end of the holding portion 56a. A small gap is provided between the distal abutment portion 56c and a tapered outer peripheral surface (inclined surface 48a2) provided at the distal end of the distal nozzle portion 48 such that the claw portions 62a and 62b, which will be described later, of the cover member 42 can reliably pass over the engagement projected portion 48a of the distal nozzle portion 48 at the time of assembly.

Figure 5:
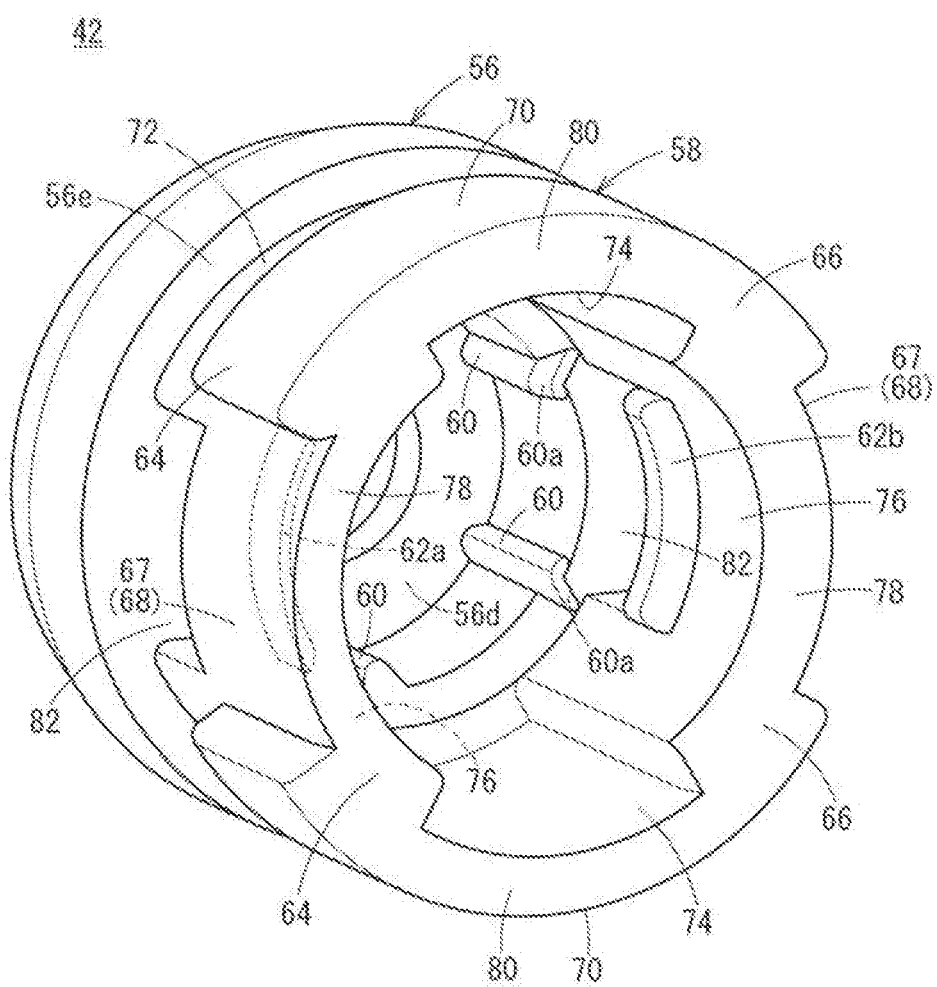
FIG. 5 is a perspective view of the cover member viewed from the proximal side.

As illustrated in FIG. 5, the base portion 56 further includes a plurality of ribs 60 that protrude from an inner peripheral surface of the holding portion 56a, extend along the axis of the cap 40, and fit with the outer peripheral surface of the seal member 41. The plurality of ribs 60 are provided at equal intervals in the circumferential direction on the inner peripheral surface of the holding portion 56a. Each of distal ends of the plurality of ribs 60 is connected to the distal wall 56d of the base portion 56. Each of the plurality of ribs 60 includes, at its proximal end, an inclined portion 60a whose protruding height gradually decreases toward the proximal end.

Figure 6:
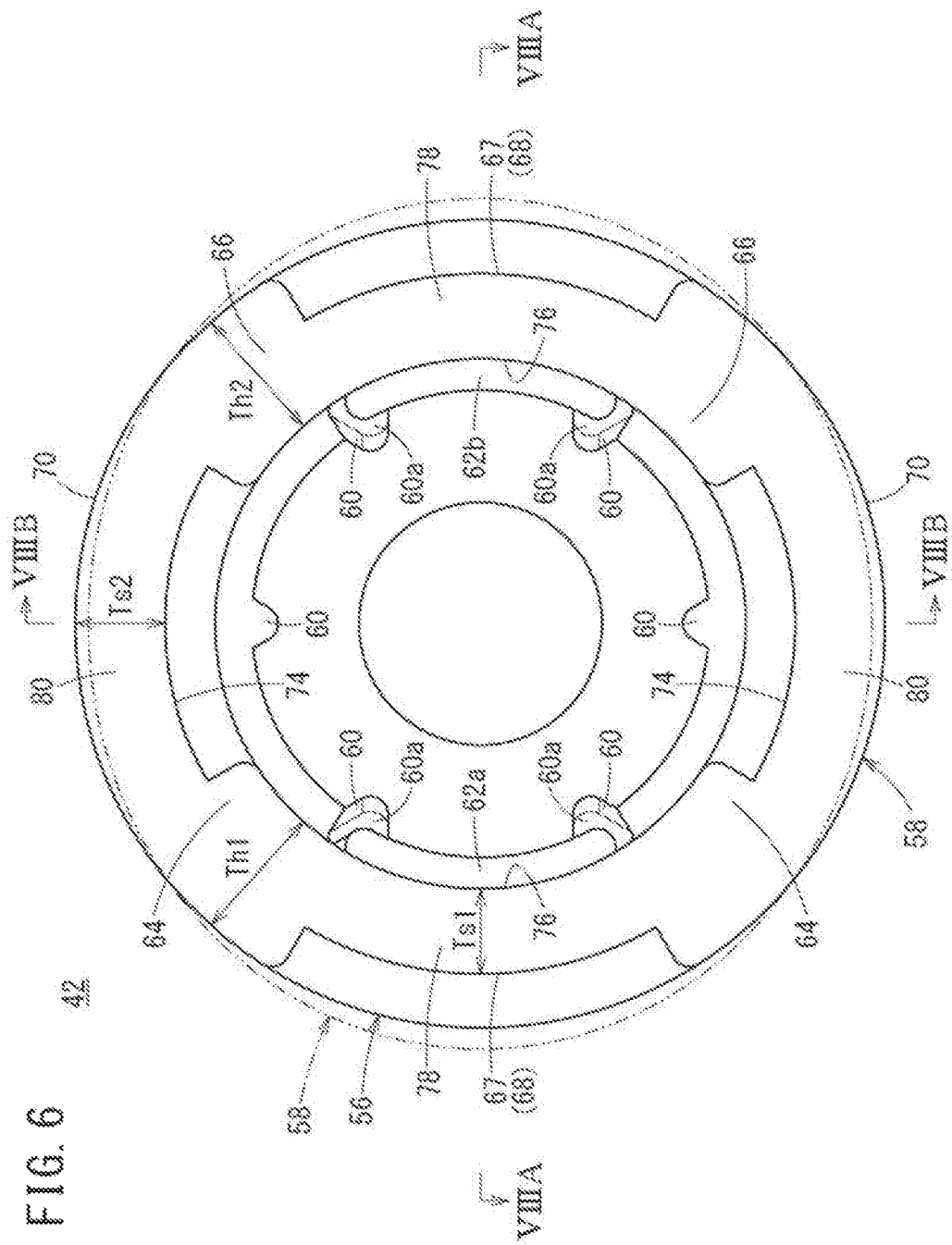
FIG. 6 is a rear view of the cover member.
Figure 7:
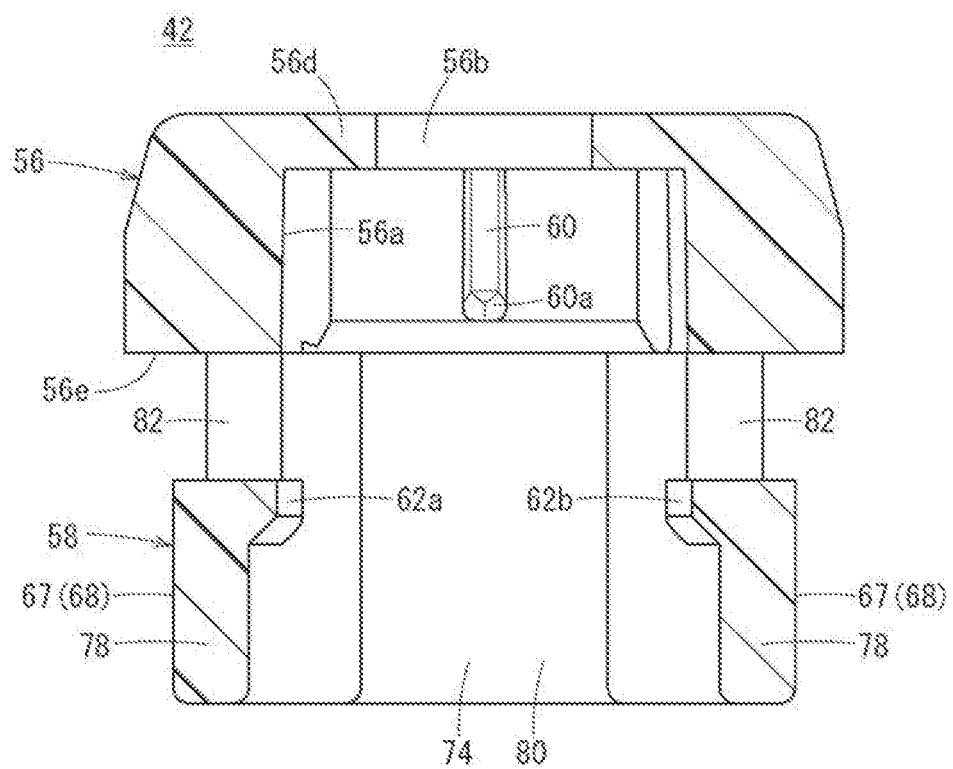
FIG. 7 is a cross-sectional view of the cover member.

As illustrated in FIGS. 5 and 6, the mounting portion 58 includes the two claw portions 62a and 62b, two first column portions 64, and two second column portions 66. The two claw portions 62a and 62b oppose each other, are arranged at positions separated from the holding portion 56a in the proximal direction, and protrude inward from an inner peripheral surface of the mounting portion 58. The cap 40 is mounted to the distal nozzle portion 48 as the two claw portions 62a and 62b engage with the engagement projected portion 48a of the distal nozzle portion 48. That is, the two claw portions 62a and 62b engage with the proximal end (locking surface 48a1) of the engagement projected portion 48a of the distal nozzle portion 48, thereby preventing the cover member 42 from coming off from the distal nozzle portion 48. Each of the two claw portions 62a and 62b extends in an arc shape in the circumferential direction along the inner peripheral surface of the mounting portion 58.

The two first column portions 64 are arranged on both sides of one claw portion 62a in the circumferential direction of the mounting portion 58, and extend in the proximal direction along the axis of the cap 40. The two first column portions 64 form two first reinforcing portions in the mounting portion 58. The two second column portions 66 are arranged on both sides of the other claw portion 62b in the circumferential direction of the mounting portion 58, and extend in the proximal direction along the axis of the cap 40. The two second column portions 66 form two second reinforcing portions in the mounting portion 58.

As illustrated in FIG. 3, inner peripheral surfaces 64a of the two first column portions 64 and inner peripheral surfaces 66a of the two second column portions 66 abut on the outer peripheral surface of the distal nozzle portion 48 (the anti-rattling projected portion 48e), thereby preventing the cap 40 from being inclined with respect to the distal nozzle portion 48.

As illustrated in FIGS. 5 and 6, an outer peripheral portion of the mounting portion 58 has two outer peripheral notch portions 67 arranged between the two first column portions 64 and between the two second column portions 66, respectively, so as to face opposite directions. Portions of the mounting portion 58 where the two outer peripheral notch portions 67 are provided have a smaller radial thickness than the two first column portions 64 and the two second column portions 66. Each distance of the two outer peripheral notch portions 67 from the axis of the distal nozzle portion 48 is shorter than a distance of each outer peripheral surface of the two first column portions 64 and the two second column portions 66 from the axis of the distal nozzle portion 48. The two outer peripheral notch portions 67 are two outer peripheral recessed portions 68.

The two outer peripheral recessed portions 68 are arranged so as to face opposite directions. One outer peripheral recessed portion 68 is arranged between the two first column portions 64. The other outer peripheral recessed portion 68 is arranged between the two second column portions 66. The two outer peripheral recessed portions 68 are recessed radially inward from the outer peripheral surfaces of the two first column portions 64 and the two second column portions 66. The two outer peripheral recessed portions 68 form first deformation promoting portions in the mounting portion 58.

The two outer peripheral recessed portions 68 extend from the respective distal ends of the two claw portions 62a and 62b to a proximal end of the mounting portion 58. Therefore, each of the two outer peripheral recessed portions 68 is open in the proximal direction on a proximal surface of the mounting portion 58. Two outer peripheral projected portions 70 are provided between the two outer peripheral recessed portions 68. Annular engagement grooves 72 are formed between each of the two outer peripheral projected portions 70 and a proximal surface 56e of the base portion 56. When the connector 18 illustrated in FIG. 1 is connected to the cap 40, engagement claws provided on an inner peripheral portion of the connector 18 engage with the annular engagement grooves 72 of the cap 40.

As illustrated in FIGS. 5 and 6, an inner peripheral portion of the mounting portion 58 includes two inner peripheral recessed portions 74. The two inner peripheral recessed portions 74 are arranged so as to face each other between the two first column portions 64 and the two second column portions 66. The two inner peripheral recessed portions 74 are recessed radially outward from the inner peripheral surfaces of the two first column portions 64 and the two second column portions 66. Each of the two inner peripheral recessed portions 74 extends from the distal end to the proximal end of the mounting portion 58. Therefore, each of the two inner peripheral recessed portions 74 is open in the proximal direction on the proximal surface of the mounting portion 58. The two inner peripheral recessed portions 74 form second deformation promoting portions of the mounting portion 58.

The inner peripheral portion of the mounting portion 58 has two proximal abutment portions 76 arranged between the two first column portions 64 and between the two second column portions 66, respectively, so as to oppose each other. The two proximal abutment portions 76 abut on the outer peripheral surface (anti-rattling projected portion 48e) of the distal nozzle portion 48 to prevent the cap 40 from being inclined with respect to the distal nozzle portion 48. The two proximal abutment portions 76 extend along the axis of the cap 40.

The mounting portion 58 includes two first side wall portions 78 having the two outer peripheral recessed portions 68, and two second side wall portions 80 having the two inner peripheral recessed portions 74, at the proximal ends of the two claw portions 62a and 62b. Each of the two first side wall portions 78 and the two second side wall portions 80 is formed in an arc shape centered on the axis of the cap 40. The two first side wall portions 78 have the same length along the circumferential direction. The two second side wall portions 80 have the same length along the circumferential direction. The length of the two first side wall portions 78 along the circumferential direction is longer than the length of the two second side wall portions 80 along the circumferential direction.

In FIG. 6, thicknesses Th1 and Th2 of the first column portion 64 and the second column portion 66 in the radial direction of the mounting portion 58 are 1.25 to 3.0 times, preferably 1.25 to 1.75 times of thicknesses Ts1 and Ts2 of the first side wall portion 78 and the second side wall portion 80 in the radial direction of the mounting portion 58. The thicknesses Ts1 and Ts2 of the first side wall portion 78 and the second side wall portion 80 are 0.5 to 1.5 mm. In the present embodiment, the radial thickness Ts1 of the two first side wall portions 78 is substantially the same as the radial thickness Ts2 of the two second side wall portions 80. Incidentally, the radial thickness Ts1 of the two first side wall portions 78 may be different from the radial thickness Ts2 of the two second side wall portions 80. The radial thicknesses Th1 and Th2 of the first column portion 64 and the second column portion 66 are 0.7 to 2.5 mm.

In the mounting portion 58, two side holes 82 radially penetrating a wall portion of the mounting portion 58 are formed on each distal side of the two first side wall portions 78 (outer peripheral recessed portions 68). Circumferential lengths of the two side holes 82 are shorter than a circumferential length of each of the two outer peripheral recessed portions 68. Incidentally, the circumferential lengths of the two side holes 82 may be equal to or longer than the circumferential length of each of the two outer peripheral recessed portions 68.

In FIG. 2, the gasket 26 liquid-tightly closes the proximal side of a lumen 13 of the syringe 24. In an initial state of the drug solution administration device 10, the gasket 26 is located on the distal side of a proximal end of the syringe 24. An outer peripheral portion of the gasket 26 is in close contact with an inner peripheral surface of the syringe 24 (body portion 44) in a liquid-tight manner. The syringe assembly 12A, the drug solution M, and the gasket 26 form a prefilled syringe 15.

The plunger assembly 14 is configured to advance the gasket 26 inside the syringe 24 and push out the drug solution M from the syringe assembly 12A. In the initial state of the drug solution administration device 10, the distal side of the plunger assembly 14 is inserted into the proximal side of the syringe 24. The drive mechanism 28 includes: a motor 31 which is driven and controlled under control action of the control unit 32 using the battery 30 as a power source; and a drive gear 37 fixed to an output shaft of the motor 31.

The chassis structure 34 is arranged inside the housing 36 (see FIG. 1). The syringe assembly 12A, the drive mechanism 28, and the plunger assembly 14 are fixed to predetermined positions of the chassis structure 34, respectively. The chassis structure 34 includes a chassis body member 34a and a motor holding member 34b that is fixed to the chassis body member 34a and holds the motor 31 against the chassis body member 34a.

The chassis body member 34a has a flange holding portion 34c that protrudes upward and holds the flange portion 54 of the syringe 24. The flange holding portion 34c is provided with a holding groove 34d into which the flange portion 54 is inserted.

In FIG. 1, the housing 36 is a hollow member configured to house the syringe assembly 12A, the gasket 26, the plunger assembly 14, the drive mechanism 28, the battery 30, the control unit 32, and the chassis structure 34 described above. The distal nozzle portion 48 of the syringe assembly 12A protrudes from the housing 36, and the cover member 42 is exposed to the outside. A window portion 36w made of a transparent material is provided on an upper surface 36a of the housing 36.

The drug solution administration device 10 can be configured as a patch type that is used by being stuck to the skin S of a patient, for example. In the case of such a patch type, a sheet-shaped sticking portion (adhesive portion) that can be stuck to the skin S is provided on a bottom surface 36b of the housing 36. In the initial state of the drug solution administration device 10, a peelable protective sheet is stuck to a sticking surface of the sticking portion.

Incidentally, the drug solution administration device 10 may be configured as a type provided with a mounting tool, such as a hook and a clip, on the bottom surface 36b of the housing 36 and attached by hooking or the like on clothes of the patient (for example, a waist portion of pants or the like).

Next, a manufacturing method (assembly method) for the syringe assembly 12A will be described.

This manufacturing method includes a syringe preparation step, a seal member preparation step, a cover member preparation step, a cap assembly step, an insertion step (FIGS. 8A and 8B), and a mounting step.

In the syringe preparation step, the syringe 24 including the distal nozzle portion 48 having the engagement projected portion 48a provided on the outer peripheral surface and the distal opening 49 is prepared.

In the seal member preparation step, the plate-shaped seal member 41 having elasticity is prepared.

In the cover member preparation step, the cover member 42, which is made of a harder material than the seal member 41 and includes the base portion 56 provided at the distal end, and the tubular mounting portion 58 extending from the base portion 56 in the proximal direction along the axis of the cap 40, is prepared, the base portion 56 including the holding portion 56a that holds the seal member 41 and the through-hole 56b that communicates with the holding portion 56a and exposes the distal surface of the seal member 41, the mounting portion 58 having the two claw portions 62a and 62b which are arranged at positions separated from the holding portion 56a in the proximal direction, protrude inward from the inner peripheral surface of the mounting portion 58, and oppose each other.

In the cap assembly step, the cap 40 is obtained by inserting the seal member 41 into the holding portion 56a of the cover member 42 and holding the seal member 41 by the holding portion 56a. When inserting the seal member 41 into the holding portion 56a of the cover member 42, the seal member 41 is guided to the holding portion 56a by the inclined portions 60a at the proximal ends of the ribs 60 provided in the holding portion 56a. Incidentally, an outer diameter of the seal member 41 is smaller than a distance between the two claw portions 62a and 62b opposing each other. For this reason, the seal member 41 can be smoothly inserted into the holding portion 56a of the cover member 42.

In the insertion step, the distal nozzle portion 48 is inserted into the mounting portion 58 of the cover member 42 in which the seal member 41 is held in the holding portion 56a as illustrated in FIGS. 8A and 8B. Incidentally, FIG. 8A is a cross-sectional view at a position corresponding to line VIIIA-VIIIA in FIG. 6, and FIG. 8B is a cross-sectional view at a position corresponding to line VIIIB-VIIIB in FIG. 6. At a completion stage of the insertion step, the two claw portions 62a and 62b do not pass over the engagement projected portion 48a of the distal nozzle portion 48, and further, the distal surface of the distal nozzle portion 48 does not abut on the seal member 41.

In the mounting step, the distal nozzle portion 48 is pushed into the mounting portion 58 from the state in FIGS. 8A and 8B until the engagement projected portion 48a passes over the two claw portions 62a and 62b toward the distal direction so as to seal the distal opening 49 of the distal nozzle portion 48 by the seal member 41, and the cap 40 is attached to the distal nozzle portion 48. When the engagement projected portion 48a passes over the two claw portions 62a and 62b, the engagement projected portion 48a deforms the first side wall portion 78 provided with the outer peripheral recessed portion 68 radially outward (see arrow A in FIG. 8A). As the first side wall portion 78 is deformed radially outward, the second side wall portion 80 provided with the inner peripheral recessed portion 74 is deformed radially inward (see arrow B in FIG. 8B). As a result, the mounting portion 58 is deformed into an elliptical shape having a long diameter in a direction in which the two first side wall portions 78 oppose each other and a short diameter in a direction in which the two second side wall portions 80 oppose each other, as indicated by the imaginary line in FIG. 6.

Next, the operation of the drug solution administration device 10 including the syringe assembly 12A configured as described above will be described.

When using the drug solution administration device 10 illustrated in FIG. 1, the administration tool 16 is connected to the drug solution administration device 10. Specifically, the connector 18 is connected to the distal nozzle portion 48 (cover member 42) of the syringe assembly 12A.

Then, the drug solution administration device 10 is attached to a patient by being stuck to the skin S of the patient or being mounted on clothes. Next, the skin S of the patient is punctured with the puncture needle 21 of the administration tool 16. Incidentally, the drug solution administration device 10 may be attached to the patient before the skin S is punctured with the puncture needle 21.

Then, when the drug solution administration device 10 receives a predetermined operation start command, the gasket 26 is pressed by the plunger assembly 14, and the gasket 26 advances inside the syringe 24, so that the drug solution M in the syringe 24 is pushed out. The drug solution M pushed out from the syringe 24 is administered (injected) into the patient's body via the administration tool 16 puncturing the patient.

The cap 40 according to the first embodiment has the following effects.

According to this cap 40, the outer peripheral portion of the mounting portion 58 has the two outer peripheral recessed portions 68, the inner peripheral portion of the mounting portion 58 has the two inner peripheral recessed portions 74, and the two claw portions 62a and 62b are provided at positions opposite to the two outer peripheral recessed portions 68, as illustrated in FIGS. 5 and 6. For this reason, when attaching the cap 40 to the distal nozzle portion 48 of the syringe 24, the mounting portion 58 is deformed outward at the two outer peripheral recessed portions 68, and is deformed inward at the two inner peripheral recessed portions 74, as illustrated in FIGS. 8A and 8B. As a result, the mounting portion 58 of the cap 40 is deformed into an elliptical shape, an excessive load is not applied to the two claw portions 62a and 62b during the assembly, and it is possible to suppress the two claw portions 62a and 62b from being partially or completely scraped off. Therefore, the cap 40 is reliably prevented from coming off from the distal nozzle portion 48 of the syringe 24. Further, the cap 40 includes the four column portions (two first column portions 64 and two second column portions 66), and thus, is barely deformed during sterilization (i.e., largely holds its shape) even when a sterilization process involving heating is performed on the syringe assembly 12A including the cap 40. For this reason, the cap 40 is reliably prevented from coming off from the distal nozzle portion 48 of the syringe 24 even after the sterilization involving heating.

As illustrated in FIG. 5, the inner peripheral portion of the mounting portion 58 has the two proximal abutment portions 76 arranged between the two first column portions 64 and between the two second column portions 66, respectively, so as to oppose each other. Then, the two proximal abutment portions 76 abut on the outer peripheral surface of the distal nozzle portion 48 to prevent the cap 40 from being inclined with respect to the distal nozzle portion 48. With this configuration, rattling of the cap 40 after the assembly can be suppressed, and thus, it is possible to suppress a variation in pressure resistance of the cap 40 (which could result in undesired leakage of the drug solution M) and a variation in pulling strength (which could result in undesired removal of the cap 40).

As illustrated in FIG. 3, the inner peripheral surfaces of the two first column portions 64 and the two second column portions 66 abut on the outer peripheral surface of the distal nozzle portion 48, thereby preventing the cap 40 from being inclined with respect to the distal nozzle portion 48. With this configuration, the rattling of the cap 40 after the assembly can be suppressed, and thus, it is possible to suppress the variation in pressure resistance of the cap 40 and the variation in pulling strength.

The base portion 56 includes the distal abutment portion 56c, which abuts on the outer peripheral surface of the distal nozzle portion 48 to prevent the cap 40 from being inclined with respect to the distal nozzle portion 48, at the proximal end of the holding portion 56a. With this configuration, the rattling of the cap 40 after the assembly can be suppressed, and thus, it is possible to suppress the variation in pressure resistance of the cap 40 and the variation in pulling strength.

As illustrated in FIG. 6, the mounting portion 58 has the two first side wall portions 78 having the two outer peripheral recessed portions 68 and the two second side wall portions 80 having the two inner peripheral recessed portions 74 at the proximal ends of the two claw portions 62a and 62b, and the thicknesses Th1 and Th2 of the first column portion 64 and the second column portion 66 in the radial direction of the mounting portion 58 are 1.25 to 3.0 times of the thicknesses Ts1 and Ts2 of the first side wall portion 78 and the second side wall portion 80 in the radial direction of the mounting portion 58. The thicknesses Th1 and Th2 are 1.25 to 1.75 times of the thicknesses Ts1 and Ts2. With this configuration, the mounting portion 58 is more likely to be deformed when the cap 40 is mounted on the distal nozzle portion 48, and is reliably prevented from coming off after the mounting of the cap 40.

The thicknesses Ts1 and Ts2 of the first side wall portion 78 and the second side wall portion 80 are 0.5 to 1.5 mm. With this configuration, the mounting portion 58 is more likely to be deformed when the cap 40 is mounted on the distal nozzle portion 48.

The thicknesses Th1 and Th2 of the first column portion 64 and the second column portion 66 are 0.7 to 2.5 mm. With this configuration, it is more difficult for the cap 40 to come off after the cap 40 is mounted on the distal nozzle portion 48.

The two outer peripheral recessed portions 68 extend from the respective distal ends of the two claw portions 62a and 62b to a proximal end of the mounting portion 58. With this configuration, the mounting portion 58 is more reliably deformed.

Each of the two inner peripheral recessed portions 74 extends from the distal end to the proximal end of the mounting portion 58. With this configuration, the mounting portion 58 is more reliably deformed.

The base portion 56 includes the plurality of ribs 60 that protrude from the inner peripheral surface of the holding portion 56a, extend along the axis of the cap 40, and fit with the outer peripheral surface of the seal member 41. Each of the plurality of ribs 60 includes, at its proximal end, an inclined portion 60a whose protruding height gradually decreases toward the proximal end. Since the plurality of ribs 60 are provided on the inner peripheral surface of the holding portion 56a, the seal member 41 can be reliably held in the holding portion 56a in the state before attaching the cap 40 to the distal nozzle portion 48 of the syringe 24, and thus, the mounting step of the cap 40 can be efficiently performed.

Second Embodiment

Figure 9:
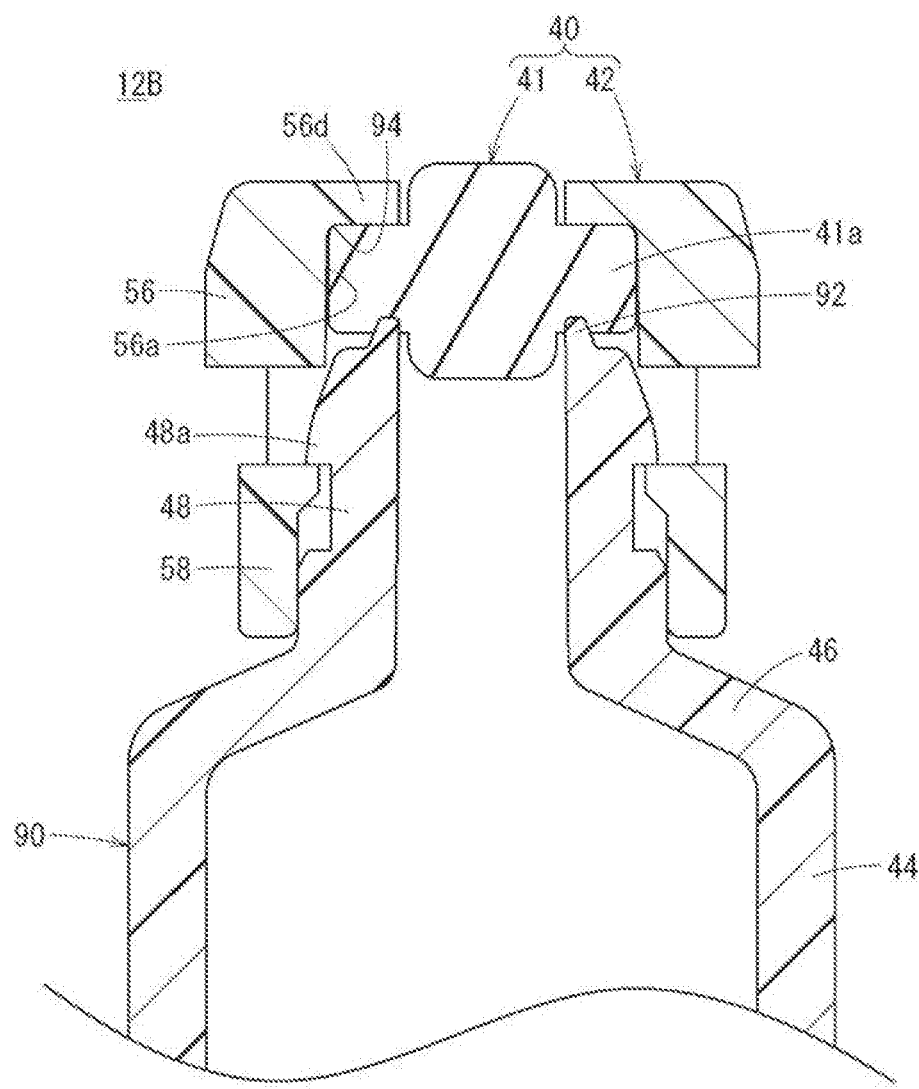
FIG. 9 is a cross-sectional view of a syringe assembly according to a second embodiment.
Figure 10:
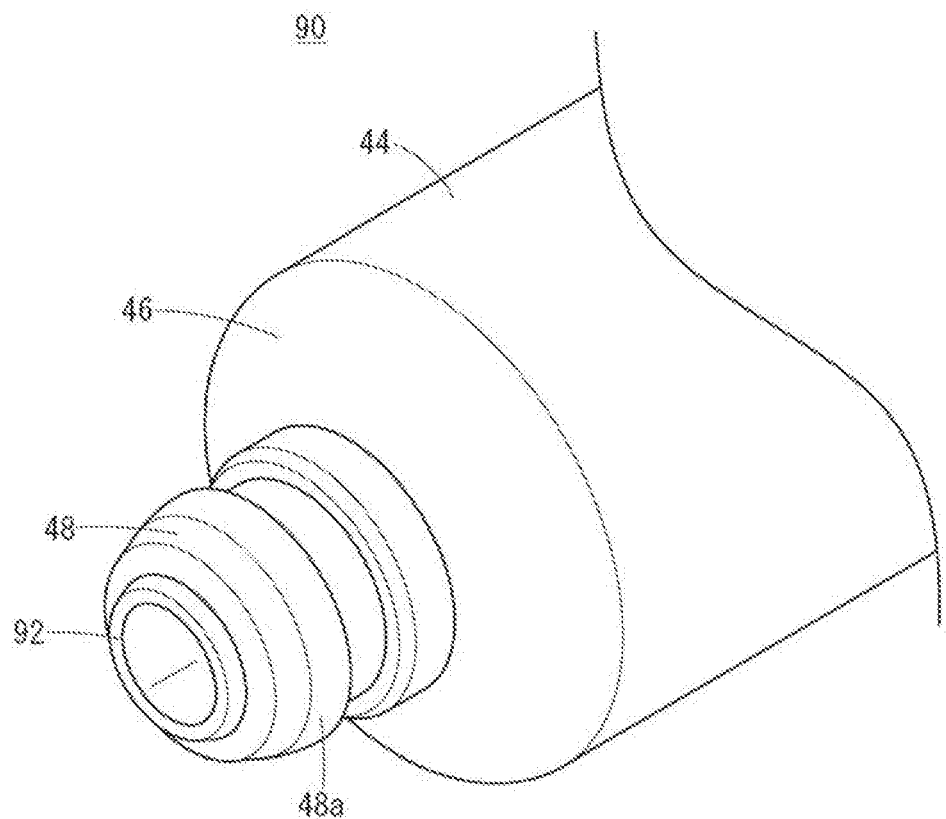
FIG. 10 is a perspective view of a distal portion of a syringe of the syringe assembly illustrated in FIG. 9.

A syringe 90 of a syringe assembly 12B according to a second embodiment illustrated in FIGS. 9 and 10 has a ring-shaped sealing protrusion 92 protruding from a distal surface of the distal nozzle portion 48. A radial width of the sealing protrusion 92 is smaller than a radial width of the distal surface of the distal nozzle portion 48. As illustrated in FIG. 9, the sealing protrusion 92 is in close contact with the seal member 41 for one round. The sealing protrusion 92 bites into the seal member 41 (seal body portion 41a) from the proximal side. Therefore, a portion of the seal member 41 into which the sealing protrusion 92 bites is recessed in the distal direction. A crush amount (axially compression amount) of the seal member 41 is the same between the first embodiment and the second embodiment.

A curved-shaped portion 94 is provided on an inner surface on the distal side of the cover member 42. Specifically, in the base portion 56 of the cover member 42, the curved-shaped portion 94 curved in an arc shape is provided at a connection site between an inner peripheral surface forming the holding portion 56a and a proximal surface of the distal wall 56d. The curved-shaped portion 94 is provided in an annular shape that makes a round about the axis of the cover member 42. The curved-shaped portion 94 functions as a reinforcing portion that increases the strength of the cover member 42. A curvature radius of the curved-shape portion 94 is set to, for example, 0.1 mm or more, preferably 0.3 mm or more. As the curvature radius increases, the strength of the cover member 42 is improved.

According to the syringe assembly 12B of the second embodiment, the sealing protrusion 92 is provided at the distal end of the distal nozzle portion 48 so that a force for crushing the seal member 41 per unit area increases, the pressure resistance is improved, and the drug solution M is reliably prevented from leaking. Further, the curved-shaped portion 94 is provided on the inner surface on the distal side of the cover member 42, and thus, damage of the cover member 42 can be suppressed even when the syringe assembly 12B is dropped with the cap 40 facing downward. That is, the drop strength (drop resistance) of the cover member 42 can be improved. In addition, the same effects as those of the first embodiment can be also obtained with the second embodiment.

Meanwhile, the pressure resistance on the distal side of the syringe assembly 12A is formed of the pressure resistance obtained by compression of the seal member 41 of the cap 40 and the pressure resistance obtained by fixation (provisional fixing) of the distal end of the distal nozzle portion 48 and the seal member 41. For this reason, when the cap 40 rotates with respect to the distal nozzle portion 48, the pressure resistance of the syringe assembly 12A is lowered as the fixation is peeled off. Therefore, if a user rotates the cap 40 by an external force at the time of connecting the connector 18 to the cap 40 during the use of the drug solution administration device 10, the pressure resistance of the syringe assembly 12A is lowered. The same also applies to the syringe assembly 12B.

Figure 11:
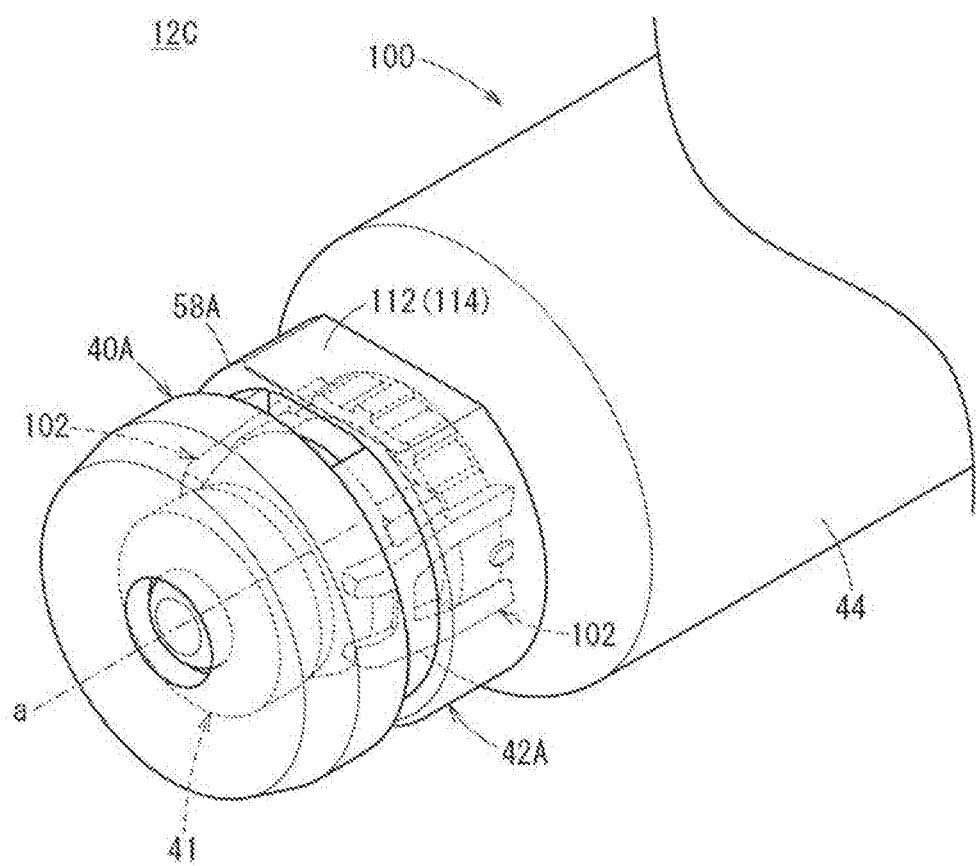
FIG. 11 is a perspective view of a syringe assembly according to a third embodiment.

In order to solve such a problem, a syringe 100 of a syringe assembly 12C according to a third embodiment illustrated in FIG. 11 and the subsequent figures has two anti-rotation projected portions 102 that prevent a cap 40A from rotating in the circumferential direction with respect to the distal nozzle portion 48. The two anti-rotation projected portions 102 are arranged on opposite sides with respect to an axis a (center axis) of the distal nozzle portion 48. Each of the anti-rotation projected portions 102 protrudes from an outer peripheral portion of the distal nozzle portion 48 to the radially outside of the distal nozzle portion 48.

As illustrated in FIG. 16B, the two anti-rotation projected portions 102 are inserted between the two first column portions 64 and the two second column portions 66, respectively, in a state where the two claw portions 62b (see FIG. 3) of the cap 40A engage with the engagement projected portions 48a of the distal nozzle portion 48 and the distal end of the distal nozzle portion 48 is in close contact with the seal member 41 (hereinafter, referred to as a "cap mounting state"), thereby opposing the inner peripheral recessed portions 74. Further, the two anti-rotation projected portions 102 engage with corner portions 64k of the two first column portions 64 and corner portions 66k of the two second column portions 66, respectively.

In the cap mounting state, ends on both sides in the circumferential direction of the anti-rotation projected portion 102 abut on the corner portion 64k of the first column portion 64 on the inner peripheral recessed portion 74 side and the corner portion 66k of the second column portion 66 on the inner peripheral recessed portion 74 side, respectively, as illustrated in FIG. 16B. Therefore, a cover member 42A of the cap 40A and the syringe 100 interfere in the circumferential direction at a total of four places in the syringe assembly 12C provided with the two anti-rotation projected portions 102 and the two inner peripheral recessed portions 74.

Figure 12:
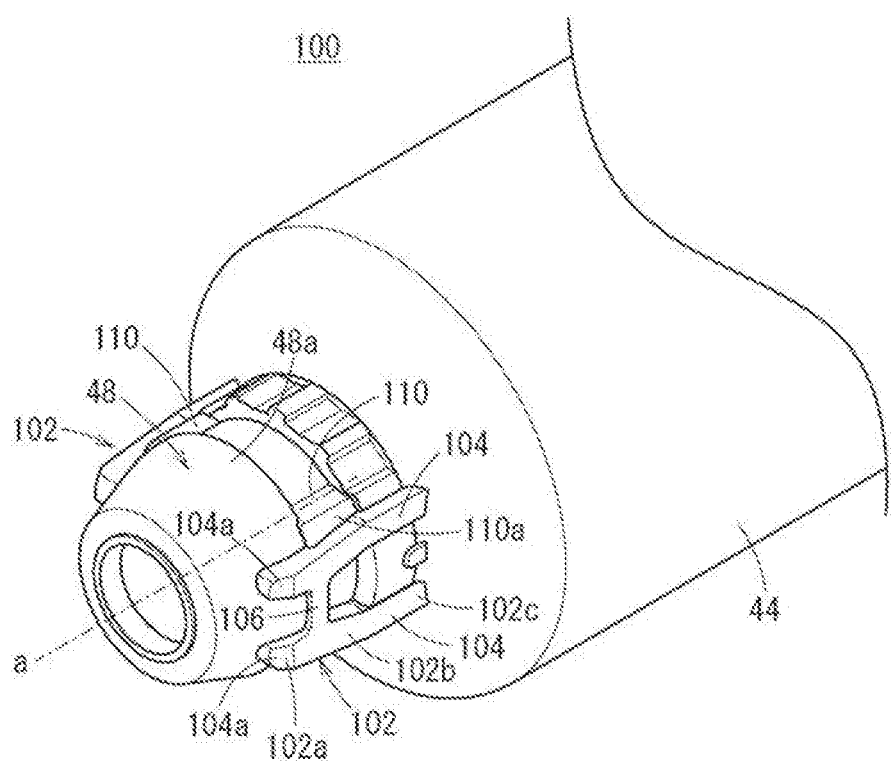
FIG. 12 is a perspective view of a syringe of the syringe assembly illustrated in FIG. 11.
Figure 13:
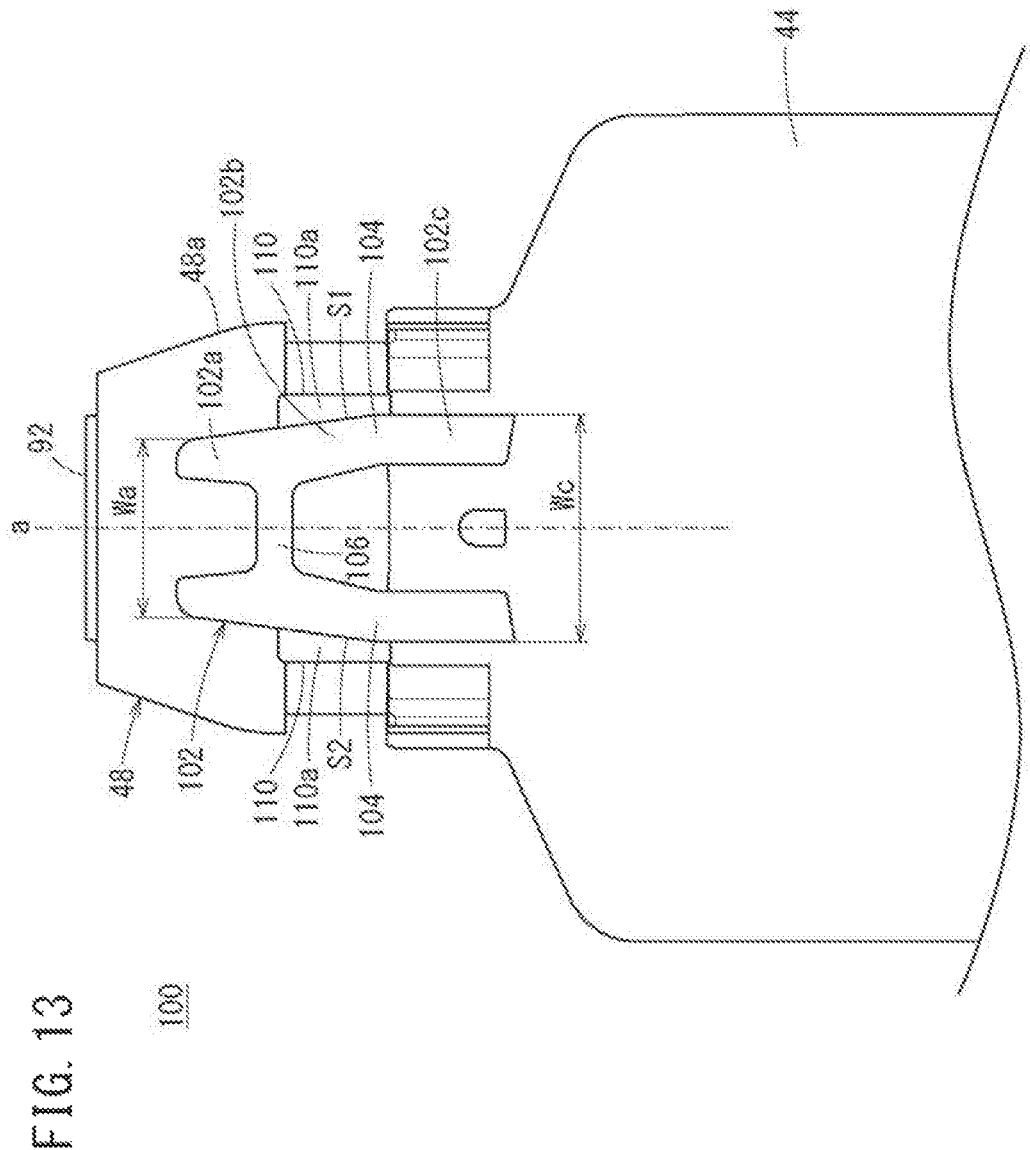
FIG. 13 is a side view of the syringe illustrated in FIG. 11.

As illustrated in FIGS. 12 and 13, the distal end of the anti-rotation projected portion 102 is located on the proximal side of the distal surface of the distal nozzle portion 48. The distal end of the anti-rotation projected portion 102 is located on the distal side of the proximal surface of the engagement projected portion 48a. In another aspect, the distal end of the anti-rotation projected portion 102 may be located at the same position as the proximal surface of the engagement projected portion 48a or on the proximal side of the proximal surface.

As illustrated in FIG. 13, the anti-rotation projected portion 102 includes: a distal projected portion 102a forming the distal side of the anti-rotation projected portion 102; a proximal projected portion 102c forming the proximal side of the anti-rotation projected portion 102; and an intermediate projected portion 102b forming a space between the distal projected portion 102a and the proximal projected portion 102c of the anti-rotation projected portion 102. A width Wc of the proximal projected portion 102c along the circumferential direction of the distal nozzle portion 48 is larger than a width Wa of the distal projected portion 102a along the circumferential direction of the distal nozzle portion 48. Further, the width Wa of the distal projected portion 102a is smaller than a corresponding width along the circumferential direction of the distal nozzle portion 48 between the first column portion 64 and the second column portion 66.

At least the intermediate projected portion 102b of the anti-rotation projected portion 102 has a portion (inclined guide portion) in which the width along the circumferential direction of the distal nozzle portion 48 increases toward the proximal direction. Specifically, the intermediate projected portion 102b has a first side surface S1 on one side in the circumferential direction and a second side surface S2 on the other side in the circumferential direction. The first side surface S1 and the second side surface S2 are inclined with respect to the axis a of the distal nozzle portion 48 so as to approach each other toward the distal direction. Further, in the circumferential direction of the distal nozzle portion 48, a distal width of a distal end of the intermediate projected portion 102b is equal to the width Wa of the distal projected portion 102a and smaller than the width between the first column portion 64 and the second column portion 66.

When the anti-rotation projected portion 102 is viewed from a direction in which the anti-rotation projected portion 102 protrudes from the distal nozzle portion 48, the anti-rotation projected portion 102 in the aspect illustrated in FIG. 13 is formed in an H shape. Therefore, the anti-rotation projected portion 102 can be also expressed as having a pair of rib-shaped portions 104 extending toward the distal end of the distal nozzle portion 48 and opposing each other with an interval in the circumferential direction, and a connecting portion 106 connecting the pair of rib-shaped portions 104. On outer surfaces of distal portions of the pair of rib-shaped portions 104, an inclined surface 104a that is inclined so as to approach the axis a of the distal nozzle portion 48 toward the distal direction is provided. In another aspect, the anti-rotation projected portion 102 may be formed in a U shape.

Figure 14:
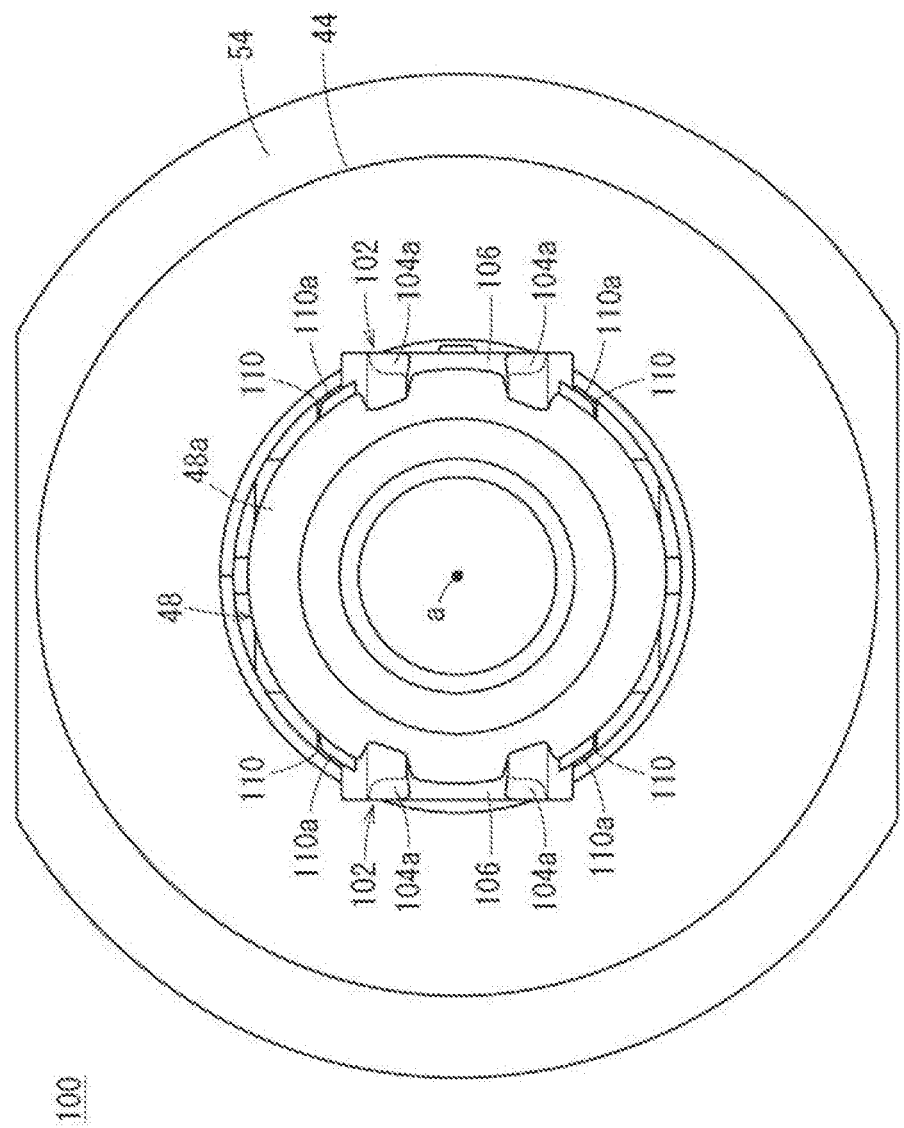
FIG. 14 is a front view of the syringe illustrated in FIG. 12 as viewed in the axial direction.

As illustrated in FIGS. 12 to 14, the syringe 100 has four fitting projected portions 110 which are adjacent to both sides of the two anti-rotation projected portions 102 in the circumferential direction of the distal nozzle portion 48. The four fitting projected portions 110 protrude radially outward from the outer peripheral portion of the distal nozzle portion 48, and fit with inner surfaces of the two first column portions 64 and inner surfaces of the two second column portions 66, respectively. An outer surface 110a (protruding end surface) of the fitting projected portion 110 extends parallel to the axis a of the distal nozzle portion 48, and is formed along an arc centered on the axis a of the distal nozzle portion 48.

A protruding height of the fitting projected portion 110 from the outer peripheral portion of the distal nozzle portion 48 is lower than a protruding height of the anti-rotation projected portion 102 from the outer peripheral portion of the distal nozzle portion 48. In the axial direction of the distal nozzle portion 48, the total length of the fitting projected portions 110 is shorter than the total length of the anti-rotation projected portions 102. A distal end of the fitting projected portion 110 is located on the proximal side of the distal end of the anti-rotation projected portion 102. A proximal end of the fitting projected portion 110 is located on the distal side of the proximal end of the anti-rotation projected portion 102.

As illustrated in FIG. 16B, an outer peripheral portion of a mounting portion 58A of the cover member 42A has two outer peripheral notch portions 112 arranged between the two first column portions 64 and between the two second column portions 66, respectively, so as to face opposite directions (see also FIG. 11). Portions of the mounting portion 58A where the two outer peripheral notch portions 112 are provided have a smaller radial thickness than the two first column portions 64 and the two second column portions 66. Each distance of the two outer peripheral notch portions 112 from the axis a of the distal nozzle portion 48 is shorter than a distance of each outer peripheral surface of the two first column portions 64 and the two second column portions 66 from the axis a of the distal nozzle portion 48. The two outer peripheral notch portions 112 are two flat portions 114 parallel to the axis of the cap 40A.

With the syringe assembly 12C according to the third embodiment configured as described above, the anti-rotation projected portions 102 of the syringe 100 oppose the inner peripheral recessed portions 74 of the cap 40A in the cap mounting state as illustrated in FIGS. 16A and 16B, and engage with the corner portions 64k of the two first column portions 64 and the corner portions 66k of the two second column portions 66, respectively. For this reason, the rotation of the cap 40A with respect to the distal nozzle portion 48 is prevented. Therefore, the cap 40A does not rotate by an external force when a user connects the connector 18 to the cap 40A, and the fixation between the seal member 41 and the distal nozzle portion 48 is not peeled off. Accordingly, it is possible to maintain the fixation of the seal member 41 and prevent a decrease in pressure resistance of the syringe assembly 12C.

The syringe 100 includes the four fitting projected portions 110 which are adjacent to both the sides of the two anti-rotation projected portions 102 in the circumferential direction of the distal nozzle portion 48, protrude radially outward from the outer peripheral portion of the distal nozzle portion 48, and fit with the inner surfaces of the two first column portions 64 and the inner surfaces of the two second column portions 66, respectively. With this configuration, the four fitting projected portions 110 interfere with the inside of the cover member 42A of the cap 40A (a portion of the inner surface of the cover member 42A that is adjacent to the inner peripheral recessed portion 74) in the provisionally assembled state before reaching the cap mounting state in the cap mounting step as illustrated in FIGS. 15A and 15B. Due to this interference, the axis of the cap 40A and the axis a of the distal nozzle portion 48 are aligned with each other in the provisionally assembled state before reaching the cap mounting state. Then, as the cap 40A is further pushed in the proximal direction, the cap mounting state illustrated in FIG. 16A can be achieved with the axis of the cap 40A and the axis a of the distal nozzle portion 48 being aligned For this reason, the inclination of the cap 40A at the time of connecting the connector 18 (see FIG. 1) to the cap 40A can be prevented, and the lateral displacement of the seal member 41 can be prevented. That is, it is possible to prevent the fixation of the seal member 41 from being peeled off due to the connection of the connector 18.

As illustrated in FIG. 13, the anti-rotation projected portion 102 includes: a distal projected portion 102a forming the distal side of the anti-rotation projected portion 102; a proximal projected portion 102c forming the proximal side of the anti-rotation projected portion 102; and an intermediate projected portion 102b forming a space between the distal projected portion 102a and the proximal projected portion 102c of the anti-rotation projected portion 102. The width Wc of the proximal projected portion 102c along the circumferential direction of the distal nozzle portion 48 is larger than the width Wa of the distal projected portion 102a along the circumferential direction of the distal nozzle portion 48, and at least the intermediate projected portion 102b of the anti-rotation projected portion 102 has a portion (inclined guide portion) in which the width along the circumferential direction of the distal nozzle portion 48 increases toward the proximal direction. Further, in the circumferential direction of the distal nozzle portion 48, the distal widths of the distal ends of the two intermediate projected portions 102b are equal to the widths Wa of the corresponding two distal projected portions 102a, and are smaller than the corresponding widths between each of the two first column portions 64 and each of the two second column portions 66. With this configuration, when the cap 40A is mounted to the distal nozzle portion 48 in the assembly step of the syringe assembly 12C, the anti-rotation projected portion 102 is likely to be inserted between the first column portion 64 and the second column portion 66 of the cap 40A. Therefore, it is possible to improve the ease of assembly at the time of mounting the cap.

The detailed description above describes embodiments of a cap, syringe assembly and manufacturing method representing examples of the cap, syringe assembly and manufacturing method disclosed here. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

For example, almost all of the two anti-rotation projected portions may have two intermediate projected portions, that is, inclined guide portions. In this case, inclined surfaces, which are inclined so as to approach the axis of the distal nozzle portion, may be provided at the distal ends of the two intermediate projected portions, respectively.

What is claimed is:

1. A tubular cap mountable to a distal nozzle portion of a syringe, the cap comprising:
a plate-shaped seal member that has elasticity and seals a distal opening of the distal nozzle portion; and
a tubular cover member that holds the seal member and is harder than the seal member, wherein
the cover member has a base portion provided at a distal end of the cover member, and a tubular mounting portion that extends in a proximal direction from the base portion along an axis of the cap and covers the distal nozzle portion,
the base portion has a holding portion that holds the seal member, and a through-hole that communicates with the holding portion and exposes a distal surface of the seal member,
the mounting portion has:
two claw portions that are arranged at positions separated from the holding portion in the proximal direction, protrude inward from an inner peripheral surface of the mounting portion, and oppose each other;
two first column portions that are arranged on both sides of one of the two claw portions in a circumferential direction of the mounting portion and extend in the proximal direction along the axis of the cap; and
two second column portions that are arranged on both sides of another of the two claw portions in the circumferential direction of the mounting portion and extend in the proximal direction along the axis of the cap,
an outer peripheral portion of the mounting portion has two outer peripheral notch portions arranged between the two first column portions and between the two second column portions, respectively, so as to face opposite directions,
portions of the mounting portion where the two outer peripheral notch portions are provided have a smaller radial thickness than the two first column portions and the two second column portions, and each distance from the axis of the two outer peripheral notch portions is shorter than a distance from the axis of each outer peripheral surface of the two first column portions and the two second column portions, and
an inner peripheral portion of the mounting portion has two inner peripheral recessed portions which are arranged to oppose each other between the two first column portions and between the two second column portions, respectively, and are recessed radially outward from inner peripheral surfaces of the two first column portions and the two second column portions.

2. The cap according to claim 1, wherein
the inner peripheral portion of the mounting portion has two proximal abutment portions arranged between the two first column portions and between the two second column portions, respectively, so as to oppose each other, and
the two proximal abutment portions abut on the outer peripheral surface of the distal nozzle portion to prevent the cap from being inclined with respect to the distal nozzle portion.

3. The cap according to claim 1, wherein
the inner peripheral surfaces of the two first column portions and the two second column portions abut on the outer peripheral surface of the distal nozzle portion to prevent the cap from being inclined with respect to the distal nozzle portion.

4. The cap according to claim 1, wherein
the base portion has a distal abutment portion, which abuts on the outer peripheral surface of the distal nozzle portion to prevent the cap from being inclined with respect to the distal nozzle portion, at a proximal end of the holding portion.

5. The cap according to claim 1, wherein
the mounting portion has, at proximal ends of the two claw portions, two first side wall portions having the two outer peripheral notch portions and two second side wall portions having the two inner peripheral recessed portions, and thicknesses of the first column portion and the second column portion in a radial direction of the mounting portion are 1.25 to 3.0 times of thicknesses of the first side wall portion and the second side wall portion in the radial direction of the mounting portion.

6. The cap according to claim 5, wherein
the thicknesses of the first side wall portion and the second side wall portion are 0.5 to 1.5 mm.

7. The cap according to claim 5, wherein
the thicknesses of the first column portion and the second column portion are 0.7 to 2.5 mm.

8. The cap according to claim 1, wherein
the two outer peripheral notch portions respectively extend from distal ends of the two claw portions to a proximal end of the mounting portion.

9. The cap according to claim 1, wherein
each of the two inner peripheral recessed portions extends from the distal end to the proximal end of the mounting portion.

10. The cap according to claim 1, wherein
the base portion has a plurality of ribs which protrude from an inner peripheral surface of the holding portion, extend along the axis of the cap, and fit with an outer peripheral surface of the seal member, and
each of the plurality of ribs has, at a proximal end, an inclined portion whose protruding height gradually decreases toward the proximal end.

11. The cap according to claim 1, wherein
the two outer peripheral notch portions are two outer peripheral recessed portions which are recessed radially inward from the outer peripheral surfaces of the two first column portions and the two second column portions.

12. The cap according to claim 1, wherein
the two outer peripheral notch portions are two flat portions parallel to the axis of the cap.

13. A syringe assembly comprising: a syringe having a distal nozzle portion; and a cap mounted to the distal nozzle portion of the syringe, wherein
the cap comprises:
a plate-shaped seal member that has elasticity and seals a distal opening of the distal nozzle portion; and
a tubular cover member that holds the seal member and is harder than the seal member, wherein
the cover member has a base portion provided at a distal end of the cover member, and a tubular mounting portion that extends in a proximal direction from the base portion along an axis of the cap and covers the distal nozzle portion,
the base portion has a holding portion that holds the seal member, and a through-hole that communicates with the holding portion and exposes a distal surface of the seal member,
the mounting portion has:
two claw portions that are arranged at positions separated from the holding portion in the proximal direction, protrude inward from an inner peripheral surface of the mounting portion, and oppose each other;

two first column portions that are arranged on both sides of one of the two claw portions in a circumferential direction of the mounting portion and extend in the proximal direction along the axis of the cap; and two second column portions that are arranged on both sides of another of the two claw portions in the circumferential direction of the mounting portion and extend in the proximal direction along the axis of the cap, an outer peripheral portion of the mounting portion has two outer peripheral notch portions arranged between the two first column portions and between the two second column portions, respectively, so as to face opposite directions, portions of the mounting portion where the two outer peripheral notch portions are provided have a smaller radial thickness than the two first column portions and the two second column portions, and each distance from the axis of the two outer peripheral notch portions is shorter than a distance from the axis of each outer peripheral surface of the two first column portions and the two second column portions, and an inner peripheral portion of the mounting portion has two inner peripheral recessed portions which are arranged to oppose each other between the two first column portions and between the two second column portions, respectively, and are recessed radially outward from inner peripheral surfaces of the two first column portions and the two second column portions.

14. The syringe assembly according to claim 13, wherein the distal nozzle portion has an engagement projected portion on an outer peripheral surface, and as the claw portions of the mounting portion engages with the engagement projected portion, the cap is mounted to the distal nozzle portion, and the distal opening of the distal nozzle portion is sealed by the seal member.

15. The syringe assembly according to claim 13, wherein the syringe has two anti-rotation projected portions that prevent the cap from rotating in a circumferential direction with respect to the distal nozzle portion, and the two anti-rotation projected portions protrude from an outer peripheral portion of the distal nozzle portion to a radially outside of the distal nozzle portion, are inserted between the two first column portions and the two second column portions, respectively, and engage with corner portions of the two first column portions and corner portions of the two second column portions, respectively.

16. The syringe assembly according to claim 15, wherein the syringe has four fitting projected portions which are adjacent to both sides of the two anti-rotation projected portions in the circumferential direction of the distal nozzle portion, protrude radially outward from the outer peripheral portion of the distal nozzle portion, and fit with inner surfaces of the two first column portions and inner surfaces of the two second column portions, respectively.

17. The syringe assembly according to claim 15, wherein the two anti-rotation projected portions respectively have two distal projected portions forming distal sides of the two anti-rotation projected portions, two proximal projected portions forming proximal sides of the two anti-rotation projected portions, and two intermediate projected portions forming spaces between each of the two distal projected portions and each of the two proximal projected portions of the two anti-rotation projected portions, widths of the two proximal projected portions along the circumferential direction of the distal nozzle portion are respectively larger than widths of the two distal projected portions along the circumferential direction of the distal nozzle portion, at least the two intermediate projected portions of the two anti-rotation projected portions respectively have two inclined guide portions whose widths along the circumferential direction of the distal end nozzle portion increase toward a proximal direction, and distal widths of distal ends of the two intermediate projected portions along the circumferential direction of the distal nozzle portion and the widths of the two distal projected portions along the circumferential direction of the distal nozzle portion are smaller than corresponding widths along the circumferential direction of the corresponding distal nozzle portion between the two first column portions and the two second column portions.

18. A manufacturing method for a syringe assembly, comprising:

preparing a syringe that includes a distal nozzle portion having an engagement projected portion provided on an outer peripheral surface and a distal opening;

preparing a plate-shaped seal member having elasticity;

preparing a cover member that is made of a harder material than the seal member and includes: a base portion provided at a distal end; and a tubular mounting portion extending from the base portion in a proximal direction along an axis of a cap, the base portion having a holding portion that holds the seal member and a through-hole that communicates with the holding portion and exposes a distal surface of the seal member, the mounting portion having two claw portions that are arranged at positions separated from the holding portion in the proximal direction, protrude inward from an inner peripheral surface of the mounting portion, and oppose each other;

inserting the distal nozzle portion into the mounting portion of the cover member in which the seal member is held in the holding portion; and pushing the distal nozzle portion into the mounting portion until the engaging projected portion passes over the two claw portions toward the distal direction to seal the distal opening of the distal nozzle portion with the seal member, and mounting the cap on the distal nozzle portion, wherein the mounting portion includes: two first reinforcing portions arranged on both sides of one of the two claw portions in a circumferential direction of the mounting portion; two second reinforcing portions arranged on both sides of another of the two claw portions in the circumferential direction of the mounting portion; two first deformation promoting portions which are arranged respectively between the two first reinforcing portions and between the two second reinforcing portions and oppose each other; and two second deformation promoting portions which are arranged between each of the two first reinforcing portions and each of the two second reinforcing portions and oppose each other, and when the engagement projected portion passes over the two claw portions, the two first deformation promoting portions are deformed radially outward, and the two second deformation promoting portions are deformed radially inward so as to make a distance between the two claw portions substantially equal to an outer diameter of the engagement projected portion.

* * * * *